US009597425B2

(12) United States Patent
Olson et al.

(10) Patent No.: US 9,597,425 B2
(45) Date of Patent: Mar. 21, 2017

(54) METHOD OF FORMING A HEMOSTATIC PRODUCT

(71) Applicant: St. Teresa Medical, Inc., Woodbury, MN (US)

(72) Inventors: Curtis E. Olson, St. Paul, MN (US); Philip A. Messina, Woodbury, MN (US); Brian Jeffrey Jackson, Woodland, MN (US)

(73) Assignee: St. Teresa Medical, Inc., Eagan, MN (US)

( * ) Notice: Subject to any disclaimer, the term of this patent is extended or adjusted under 35 U.S.C. 154(b) by 0 days.

(21) Appl. No.: 13/622,604

(22) Filed: Sep. 19, 2012

(65) Prior Publication Data

US 2013/0095229 A1 Apr. 18, 2013

Related U.S. Application Data

(60) Provisional application No. 61/548,258, filed on Oct. 18, 2011, provisional application No. 61/548,260, (Continued)

(51) Int. Cl.
*A61L 15/44* (2006.01)
*A61K 38/36* (2006.01)
(Continued)

(52) U.S. Cl.
CPC ............ *A61L 15/44* (2013.01); *A61K 9/7007* (2013.01); *A61K 38/363* (2013.01); (Continued)

(58) Field of Classification Search
CPC ........ A61M 25/02; A61M 5/00; A61M 25/10; A61F 13/00; A61K 9/00; A61K 49/00; A61K 38/19; A61K 38/18; A61K 31/727
(Continued)

(56) References Cited

U.S. PATENT DOCUMENTS 4,275,721 A * 6/1981 Olson ................... A61M 5/158
128/DIG. 26
5,447,423 A 9/1995 Fuisz et al.
(Continued)

FOREIGN PATENT DOCUMENTS

JP 2005-290610 A 10/2005
WO 99/59647 A1 11/1999
(Continued)

OTHER PUBLICATIONS

Jiang et al., "Optimization and Characterization of Dextran Membranes Prepared by Electrospinning", Biomacromolecules, 5(2):326-333 (Mar.-Apr. 2004).
(Continued)

*Primary Examiner* — Dah-Wei D Yuan
*Assistant Examiner* — Andrew Bowman
(74) *Attorney, Agent, or Firm* — Michael A. Bondi; Moss & Barnett

(57) ABSTRACT

A method of forming hemostatic sheets. Dextran and water are mixed to form a dextran-water mixture. The dextran-water mixture is formed into a first support layer. Fibrinogen and thrombin are mixed to form a fibrinogen and thrombin mixture. The fibrinogen and thrombin mixture is dispersed on the first support layer to form a hemostatic sheet.

23 Claims, 14 Drawing Sheets

Related U.S. Application Data filed on Oct. 18, 2011, provisional application No. 61/548,261, filed on Oct. 18, 2011, provisional application No. 61/585,303, filed on Jan. 11, 2012, provisional application No. 61/589,060, filed on Jan. 20, 2012.

(51) Int. Cl.

| | | |
|---|---|---|
| *A61K 38/48* | (2006.01) | |
| *A61K 47/36* | (2006.01) | |
| *A61K 9/70* | (2006.01) | |
| *A61L 15/28* | (2006.01) | |
| *A61M 5/00* | (2006.01) | |
| *A61M 25/02* | (2006.01) | |
| *A61M 25/10* | (2013.01) | |
| *A61K 49/00* | (2006.01) | |

(52) U.S. Cl.
CPC .......... *A61K 38/4833* (2013.01); *A61K 47/36* (2013.01); *A61L 15/28* (2013.01); *C12Y 304/21005* (2013.01); *A61K 49/00* (2013.01); *A61L 2300/418* (2013.01); *A61L 2400/04* (2013.01); *A61M 5/00* (2013.01); *A61M 25/02* (2013.01); *A61M 25/10* (2013.01)

(58) Field of Classification Search
USPC ................ 424/447, 423, 9.6, 85.1; 128/133; 604/509; 514/12, 2, 56
See application file for complete search history.

(56) References Cited

U.S. PATENT DOCUMENTS

| | | | |
|---|---|---|---|
| 6,116,880 A | 9/2000 | Bogue et al. | |
| 6,753,454 B1 | 6/2004 | Smith et al. | |
| 6,762,336 B1 | 7/2004 | MacPhee et al. | |
| 6,821,479 B1 | 11/2004 | Smith et al. | |
| 7,019,191 B2 | 3/2006 | Looney et al. | |
| 7,067,444 B2 | 6/2006 | Luo et al. | |
| 7,101,862 B2 | 9/2006 | Cochrum et al. | |
| 2003/0168756 A1 | 9/2003 | Balkus, Jr. et al. | |
| 2004/0018226 A1 | 1/2004 | Wnek et al. | |
| 2006/0155235 A1 | 7/2006 | Sawyer | |
| 2006/0204441 A1* | 9/2006 | Atala ................ A61K 41/0042 424/9.6 |
| 2006/0240110 A1 | 10/2006 | Kiick et al. | |
| 2006/0264130 A1 | 11/2006 | Karles et al. | |
| 2007/0160653 A1 | 7/2007 | Fischer | |
| 2007/0255238 A1 | 11/2007 | Cochrum | |
| 2008/0020015 A1 | 1/2008 | Carpenter et al. | |
| 2008/0265469 A1 | 10/2008 | Li et al. | |
| 2008/0286329 A1* | 11/2008 | Campbell ........... A61L 27/3604 424/423 |
| 2009/0053288 A1 | 2/2009 | Eskridge | |
| 2009/0177272 A1 | 7/2009 | Abbate et al. | |
| 2009/0192214 A1 | 7/2009 | Gravett et al. | |
| 2009/0291124 A1 | 11/2009 | Bedard | |
| 2010/0016802 A1* | 1/2010 | Tambourgi et al. .......... 604/179 |
| 2010/0100123 A1 | 4/2010 | Bennett | |
| 2010/0254900 A1 | 10/2010 | Campbell et al. | |
| 2011/0021964 A1 | 1/2011 | Larsen et al. | |
| 2011/0071498 A1* | 3/2011 | Hakimimehr ........ A61K 9/7007 604/509 |
| 2011/0071499 A1 | 3/2011 | Hakimimehr | |
| 2011/0112572 A1 | 5/2011 | Miller | |
| 2011/0125089 A1 | 5/2011 | Senderoff et al. | |
| 2011/0150973 A1* | 6/2011 | Bowlin et al. ................ 424/447 |
| 2011/0250257 A1 | 10/2011 | Arthur | |

FOREIGN PATENT DOCUMENTS

| | | |
|---|---|---|
| WO | 0033744 A1 | 6/2000 |
| WO | 2006119487 A1 | 9/2006 |

OTHER PUBLICATIONS

Jiang et al., "Modulation of Protein Release from Biodegradable Core—Shell Structured Fibers Prepared by Coaxial Electrospinning", Journal of Biomedical Materials Research Part B: Applied Biomaterials, 79B(1);50-57 (Oct. 2006).
Notification of Transmittal of The International Search Report and the Written Opinion of the International Searching Authority, or the Declaration (PCT/12/60643) mailed Dec. 20, 2012 (10 pages).
Communication regarding Extended European Search Report, Appln. No. 12841666.6, dated Apr. 7, 2015, 8 pages.
International Preliminary Report on Patentability (Chapter I of the Patent Cooperation Treaty (May 1, 2014), USPTO.
Stephen W. Rothwell et al., "The long term immunological response of swine after two exposures to a salmon thrombin and fibrinogen hemostatic bandage", Biologicals, vol. 38, No. 6, Nov. 1, 2010, pp. 619-628, XP055178774, ISSN: 1045-1056, DOI: 10.1016/j.biologicals.2010.07.001.
European Office Action 94(3) for EP App. No. 12842651.7 dated Dec. 13, 2016, 6 pgs.

\* cited by examiner

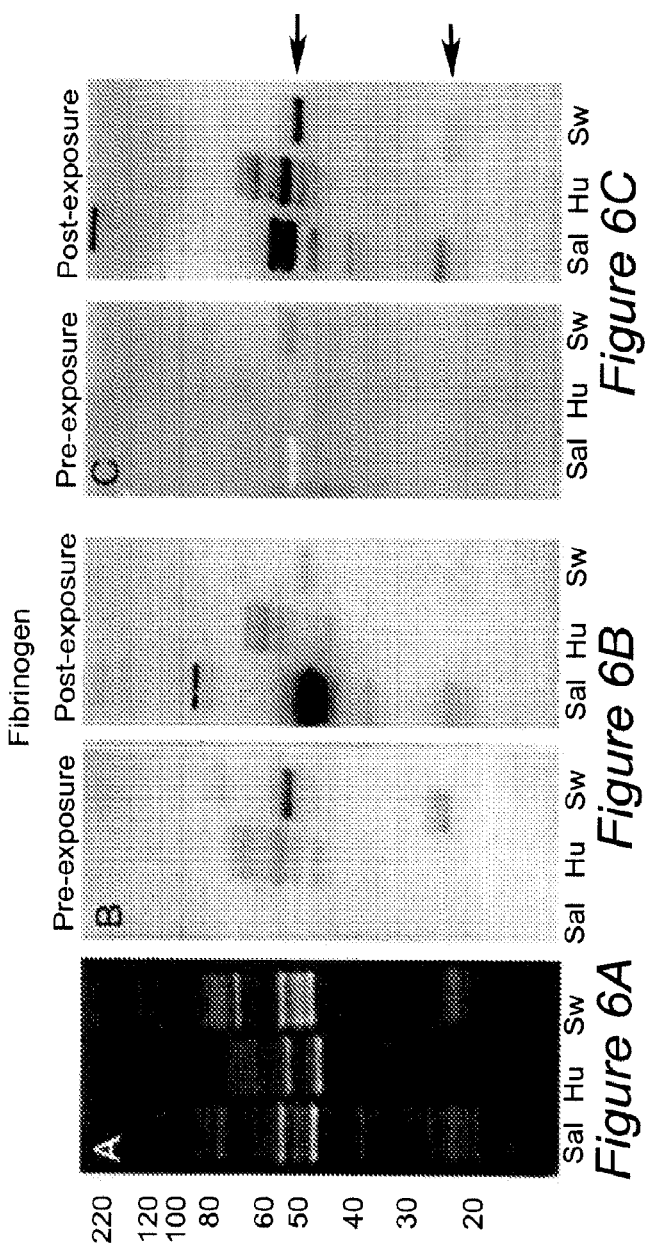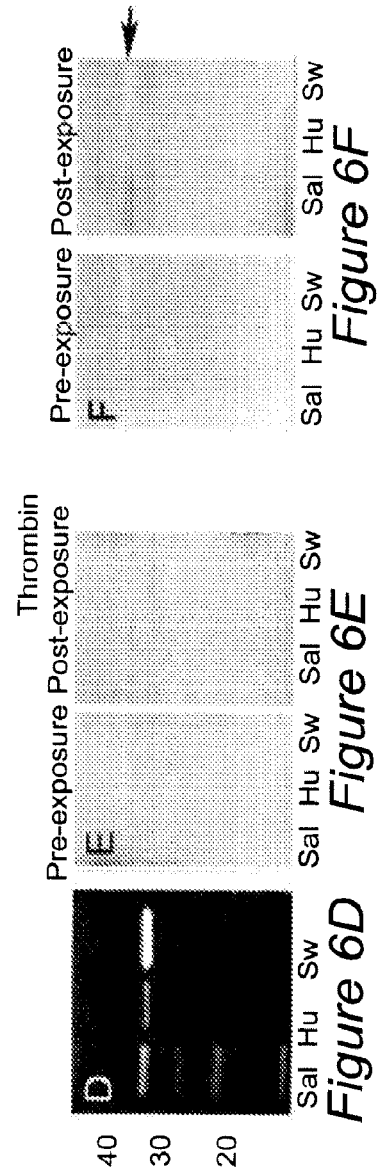

METHOD OF FORMING A HEMOSTATIC PRODUCT

REFERENCE TO RELATED APPLICATION

This application claims priority to U.S. Provisional Application Nos. 61/548,258, which was filed on Oct. 18, 2011; 61/548,260, which was filed on Oct. 18, 2011; 61/548,261, which was filed on Oct. 18, 2011; 61/585,303, which was filed on Jan. 11, 2012; 61/589,060, which was filed on Jan. 20, 2012, the contents of which are incorporated herein by reference.

FIELD OF THE INVENTION

The invention relates generally to products having hemostatic characteristics. More particularly, the invention relates to a method of forming dextran and thrombin sheets that are suitable for use in hemostatic applications.

BACKGROUND OF THE INVENTION

The body's natural response to stem bleeding from a wound is to initiate blood clotting via a complex process known as the coagulation cascade. The cascade involves two pathways that ultimately lead to the production of the enzyme thrombin, which catalyzes the conversion of fibrinogen to fibrin.

Fibrin is then cross-linked to form a clot, resulting in hemostasis. For wounds that are not severe, and in individuals that have no countervening conditions, the body is usually able to carry out this process efficiently in a manner that prevents excessive loss of blood from the wound. However, in the case of severe wounds, or in individuals in whom the clotting mechanism is compromised, this may not be the case.

For such individuals, it is however possible to administer components of the coagulation cascade, especially thrombin and fibrinogen, directly to the wound to bring about hemostasis. Bandaging of bleeding wounds is also a usual practice, in part to isolate and protect the wounded area, and also to provide a means to exert pressure on the wound, which can also assist in controlling bleeding.

While these methods may be carried out satisfactorily in cases of mild trauma or under conditions of "controlled" wounding (e.g. surgery), many situations in which such treatments are most needed are also those in which it is the most difficult to provide them. Examples of such wounds include, for example, those inflicted during combat, or unanticipated wounds that occur as the result of accidents. In such circumstances, survival of the wounded individual may depend on stopping blood loss from the wound and achieving hemostasis during the first few minutes after injury. Unfortunately, given the circumstances of such injuries, appropriate medical intervention may not be immediately available.

In particular, the treatment of penetrating wounds such as bullet wounds or some wounds from shrapnel is problematic. This is due to the difficulty in placing a bandage and/or therapeutic agents at the actual site of injury, which includes an area that is well below the body surface and difficult or impossible to access using conventional techniques.

Jiang et al. in Biomacromolecules, v. 5, p. 326-333 (2004) teaches electrospun dextran fibers. Agents associated with the fibers (e.g. BSA, lysozyme) are directly electrospun into the fibers. The fibers may also include other polymers electrospun with the dextran.

Jiang et al. in Journal of Biomedical Materials Research Part B: Applied Biomaterials, p. 50-57 (2006) discloses electrospun fibers that are a composite of poly(c-caprolactone) as a shell and dextran as a core. These fibers provide the slow release of agents (bovine serum albumin, BSA) that are also electrospun into the fibers.

Smith et al., U.S. Pat. No. 6,753,454, discloses electrospun fibers comprising a substantially homogeneous mixture of a hydrophilic polymer and a polymer that is at least weakly hydrophobic, which may be used to form a bandage. The bandage may comprise active agents (e.g. dextran). However, the disclosed fibers are not readily soluble in liquid.

MacPhee et al., U.S. Pat. No. 6,762,336, teaches a hemostatic multilayer bandage that comprises a thrombin layer between two fibrinogen layers. The bandage may contain other resorbable materials such as glycolic acid or lactic acid based polymers or copolymers. Neither electrospun fibers nor dextran fibers are taught as components of the bandage.

Smith et al., U.S. Pat. No. 6,821,479, teaches a method of preserving a biological material in a dry protective matrix, the matrix comprising fibers such as electrospun fibers. One component of the fibers may be dextran, but homogeneous dextran fibers are not described.

Cochrum et al., U.S. Pat. No. 7,101,862, teaches hemostatic compositions and methods for controlling bleeding. The compositions comprise a cellulose containing article (e.g. gauze) to which a polysaccharide is covalently or ionically crosslinked. The crosslinked polysaccharide may be dextran. However, the compositions are not electrospun and exogenous clotting agents are not included in the compositions.

Wnek et al., U.S. Patent Publication No. 2004/0018226, discloses fibers produced by an electroprocessing technique such as electrospinning. The fibers comprise enclosures within the fibers for containing substances that are not miscible with the fibers. Dextran is not taught as a fiber component.

Fisher et al., U.S. Patent Publication No. 2007/0160653, teaches a hemostatic textile comprising hemostatic factors (e.g. thrombin, fibrinogen) but the fibers are formed from electrospun glass plus a secondary fiber (e.g. silk, ceramic, bamboo, jute, rayon, etc.)

Carpenter et al., U.S. Patent Publication No. 2008/0020015, teaches wound dressing comprised of various biodegradable polymers and hydrogels having allogenic or autologous precursor cells (e.g. stem cells) dispersed within the polymers. The polymers may be prepared by electrospinning, and one polymer component may be dextran. However, the polymers cannot be immediately soluble upon contact with liquid, as they must provide a scaffolding for delivery of the cells over time, even though the polymers eventually biodegrade in situ.

Li et al., U.S. Patent Publication No. 2008/0265469, describes electrospun nanofibers that may include dextran. However, the nanofibers are not described as readily soluble in liquids.

Eskridge et al., U.S. Patent Publication No. 2009/0053288, teaches a woven hemostatic fabric comprised of about 65% fiberglass yarn and about 35% bamboo yarn. The fiberglass component may be electrospun, and hemostatic factors such as thrombin may be associated with the fabric, e.g. by soaking the material in a solution of thrombin. This document indicates that dextran may be added as a hygroscopic agent.

There is an ongoing need to provide improved methods and means to initiate blood clotting in wounds to stop or at least slow blood loss. In particular, there is an ongoing need to improve the capability to readily promote hemostasis in severe wounds in a facile manner, especially under circumstances where immediate treatment by medical personnel is limited or unavailable.

Bowlin et al., U.S. Patent Publication No. 2011/0150973, discloses a method of delivering one or more agents of interest to a location of interest. The method includes applying or delivering to a location of interest a hemostatic hemostatic product. The hemostatic hemostatic product includes electrospun dextran fibers that dissolve upon contact with liquid. The hemostatic hemostatic product also includes one or more agents of interest associated with said electrospun dextran fibers. Applying or delivering results in dissolution of the electrospun dextran fibers in liquid at the location of interest to thereby release the one or more agents of interest into the liquid.

SUMMARY OF THE INVENTION

An embodiment of the invention is directed to a method of forming hemostatic sheets. Dextran and water are mixed to form a dextran-water mixture. The dextran-water mixture is formed into a first support layer. Fibrinogen and thrombin are mixed to form a fibrinogen and thrombin mixture. The fibrinogen and thrombin mixture is dispersed on the first support layer to form a hemostatic sheet.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 6A-F. Qualitative assessment of immunoglobulin production by swine in response to salmon proteins by Western blotting. (A) PAGE of salmon (Sal), human (Hu) and swine (Sw) fibrinogen preparations and corresponding Western blots with serum from two animals (B and C). Serum from pre-exposure and final euthanasia blood draws are presented in these panels. IgG isotypes present in the serum were visualized by specific HRP anti-swine IgG second antibodies and are detected as binding to the proteins in the gel samples. Arrows indicate the positions of the IgG heavy and light chains components in the swine protein lanes which are also recognized by the 2nd antibody. Molecular weights are show to the left (kDal$\times 10^{-3}$). (D) PAGE of salmon (Sal), human (Hu) and swine (Sw) thrombin preparations and corresponding Western blots with serum from the same animals shown in (C and D). In these animals, thrombin was not recognized in E, but there is a faint reaction in the salmon protein lane in F (arrow). The camera in the detection system detected the heavy swine thrombin protein on the membrane as a white band in F.

DETAILED DESCRIPTION OF THE PREFERRED EMBODIMENTS

Figure 1:
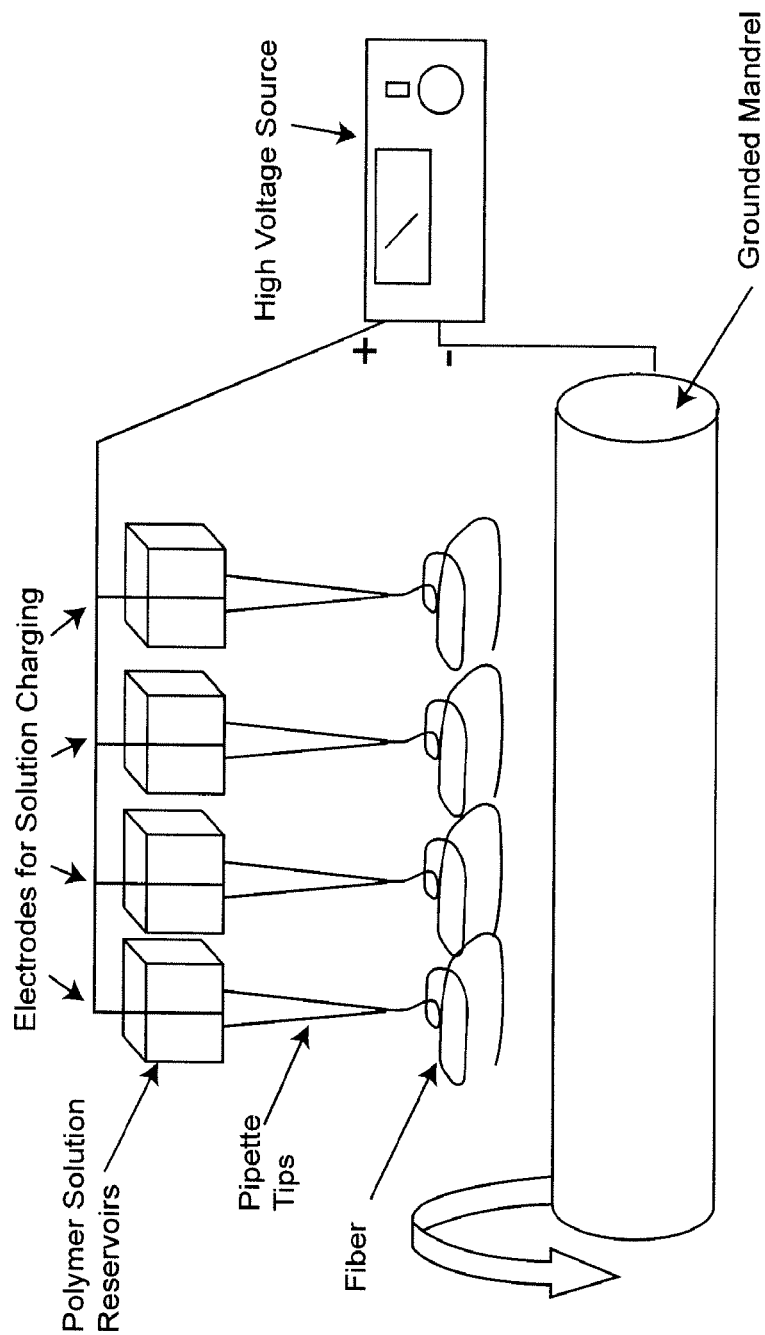
FIG. 1. Schematic of the electrospinning apparatus. The key elements of the electrospinning system include a high voltage power supply, a source reservoir for the polymer and a grounded mandrel. This system utilizes a cylindrical target mandrel; however the electrospinning process can be adapted to produce much more complex shapes. Single and/or multiple polymers can be independently or simultaneously delivered to the electric field from one or more source reservoirs. Electrospinning distinct and unique polymers from separate sources in a temporal sequence can be used to produce a laminated structure.

An embodiment of the invention is directed to a process of forming a hemostatic product from a plurality of sheets hemostatic material. As an initial step in forming the hemostatic product, the sheets of hemostatic material are prepared.

The sheets have a relatively uniform thickness and appearance. Forming the sheets with a relatively uniform thickness and appearance enhances the ability to accurately use the hemostatic products to treat the particular injury.

When the hemostatic product is applied to the injury site, the materials used to fabricate the hemostatic product dissolve to thereby release the materials to the injury site and provide the hemostatic effect.

In one embodiment, the site of action is a wound bed, and the active agents that are delivered by the hemostatic product are factors or agents that participate in the coagulation cascade such as thrombin and fibrinogen. Application of the hemostatic product to a wound results in dissolution of the dextran fibers in blood within the wound bed, which in turn results in release or delivery of the active agents at or into the site.

Thrombin and fibrinogen that are associated with the hemostatic product are in forms that are biologically active when they come into contact with blood. Hence, upon dissolution, the thrombin acts on the fibrinogen, converting it to fibrin, which then forms a clot within the wound, staunching the flow of blood.

This invention uses layers that provide a product that is easier to commercialize and provides a more uniform dispersion of the components in the hemostatic product.

The invention provides dextran fibers, especially electrospun dextran fibers. The electrospun dextran fibers may be formed into a variety of hemostatic products for a variety of purposes. Generally, one or more substances of interest are associated with the electrospun dextran fibers in the hemostatic product such as for the purpose of delivering the one or more substances of interest to a liquid of interest. Upon contact with the liquid, the electrospun dextran fibers dissolve in a relatively short period of time and the associated substances are released into the liquid milieu.

In one embodiment of the invention, the electrospun dextran fibers are formed into a hemostatic product. The hemostatic product generally includes active agents associated with the electrospun dextran fibers, the active agents being delivered to a site of action (e.g. a wound) via application of the hemostatic product to the site.

The site of action contains or will contain a liquid, and when the hemostatic product is applied to the site of action, the electrospun dextran fibers in the hemostatic product dissolve in the liquid, and the active agents associated with or sequestered in or around the mat of dextran fibers are released into the liquid.

In one embodiment, the site of action is a wound bed, and the active agents that are delivered by the hemostatic product are factors or agents that participate in the coagulation cascade such as thrombin and fibrinogen. Application of an electrospun dextran fiber hemostatic product to a wound results in dissolution of the dextran fibers in blood within the wound bed, which in turn results in release or delivery of the active agents at or into the site.

Thrombin and fibrinogen that are associated with the hemostatic product are in forms that are biologically active when they come into contact with blood. Hence, upon dissolution, the thrombin acts on the fibrinogen, converting it to fibrin, which then forms a clot within the wound to thereby staunch the flow of blood.

In some embodiments of the invention, only spun dextran fibers are utilized and thus after clot formation, there is no need to disturb the clot to remove hemostatic product components, since none remain at the site. In other embodiments, as described below, the hemostatic product may include other materials such as support or backing material, which, after initial rapid application of the hemostatic product, may later be removed for further treatment of the wound by conventional methods.

Electrospinning is a non-mechanical processing strategy and can be scaled to accommodate the large volumes necessary to meet the needs of commercial processing. A schematic representation of one type of set-up for electrospinning is provided in FIG. 1. In this process a polymer solution, or melt, is injected with current to create a charge imbalance. The charged solution is then placed in proximity to a grounded target (in FIG. 1, a grounded mandrel).

At a critical voltage the charge imbalance begins to overcome the surface tension of the polymer source, forming an electrically charged jet. Within the electric field, the jet is directed towards the grounded target and the carrier solvent evaporates. Depending upon reaction conditions, and the polymers used in the process, electrospinning can be utilized to produce a fine aerosol of material or a continuous nonwoven mat of fibrillar material, as shown in FIG. 1.

For many polymers, the nature of the electrospinning process intrinsically provides a high degree of control over the diameter of the resulting fibers. Micron to nanoscale diameters can be selectively achieved simply by regulating the starting concentrations of the polymers present in the electrospinning solutions. By controlling the motion of the ground target with respect to the source solution, fibrils may be deposited into a random matrix or into aligned arrays that are oriented along a defined axis.

Figure 2A:
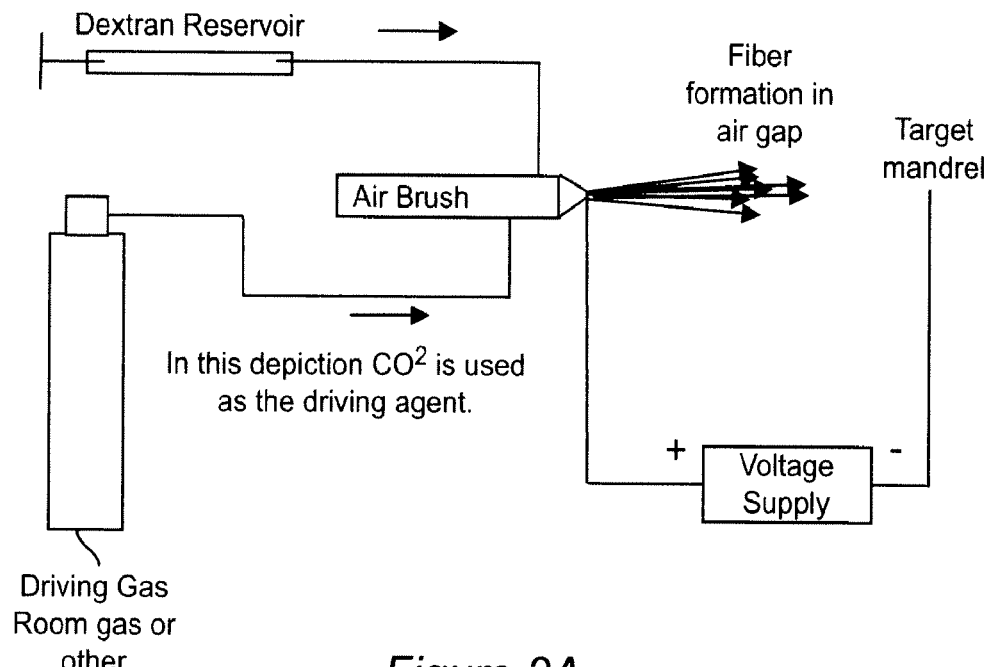
FIGS. 2A and B. A, schematic of air brush based dextran processing; B, dextran fibers produced by electroaerosol processing. The amount of material depicted is probably enough material for about two hemostatic products. Note the loft of the material. An electric field was used to target the dextran to the mandrel.

A second schematic of an electrospinning apparatus is shown in FIG. 2A. The key elements of the electrospinning system include a high voltage power supply, a source reservoir for the polymer and a grounded target mandrel. The system that is depicted utilizes a cylindrical target mandrel; however the electrospinning process can be adapted to produce much more complex shapes.

Figure 2B:
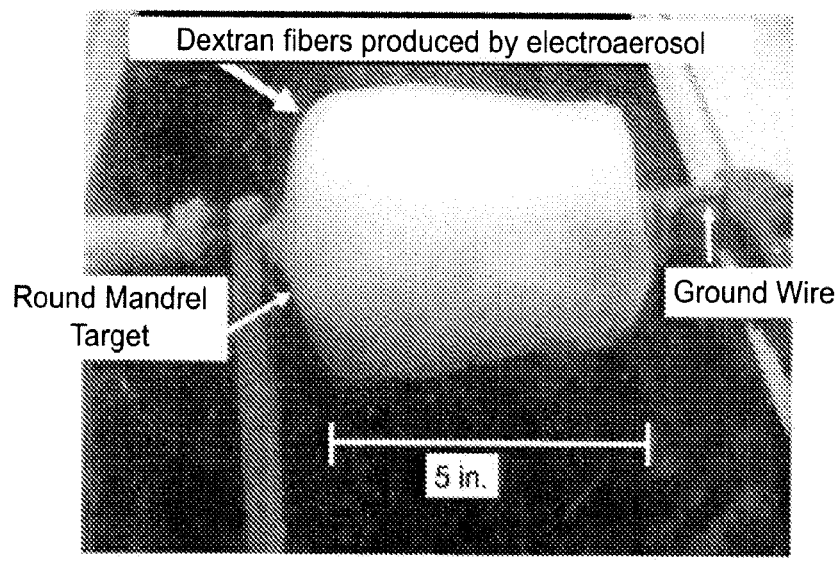
Figure 3:
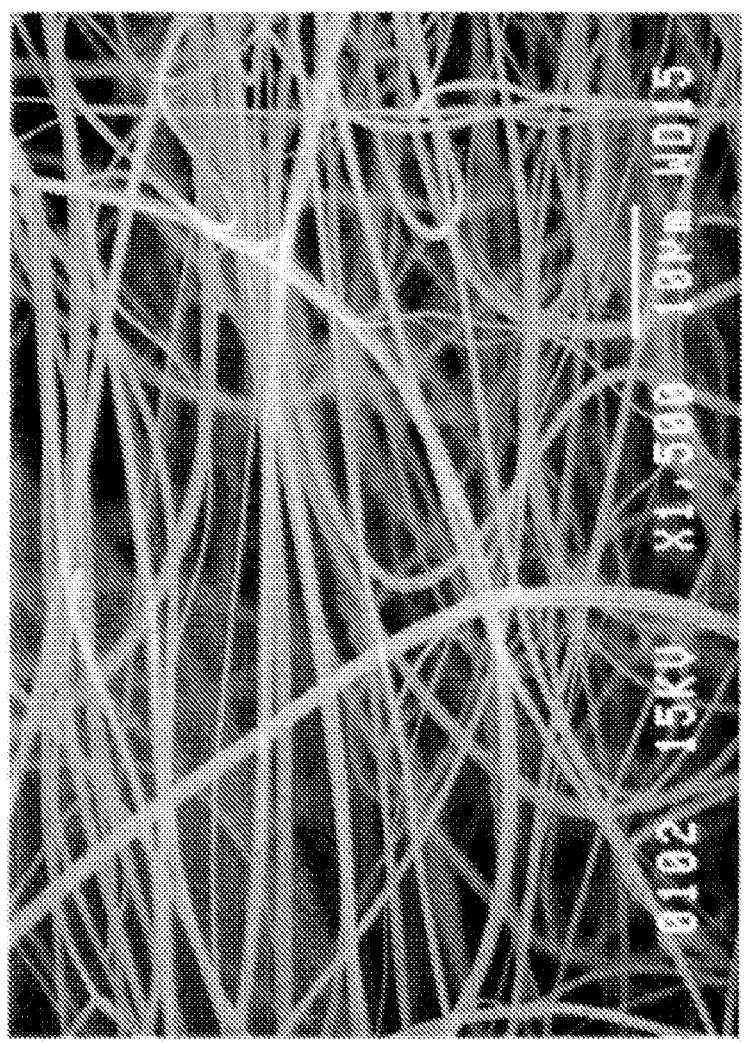
FIG. 3. Scanning electron micrograph of electrospun dextran fibers. The nominal average cross sectional diameter of the individual fibers was 1 micron, providing a large surface area.

Single and/or multiple polymers can be independently or simultaneously delivered to the electric field from one or more source reservoirs. In addition, electrospinning distinct and unique polymers from separate sources in a temporal sequence can be used to produce a laminated structure. FIG. 2B shows the result of electrospinning about 10 grams of dextran dissolved in deionized water onto a round mandrel target, as described in detail in the Example 1 below. FIG. 3 shows a scanning electron micrograph of electrospun dextran fibers in which the average cross sectional diameter of the individual fibers is about 1 micron.

Those of skill in the art will recognize that electrospinning is not the only way to make dextran fibers. Such fibers may be produced by other methods of aerosolization. However, the electric field helps in the efficient collection of the fibers, and electrospinning may yield more uniform fibers. Other technologies which might also be employed for spinning dextran fibers, including those described in Luo et al., U.S. Pat. No. 7,067,444; Bogue et al., U.S. Pat. No. 6,116,880; and Fuisz et al., U.S. Pat. No. 5,447,423, the complete contents of each of which are hereby incorporated by reference.

In particular, so-called "cotton-candy machines" (with or without applied electrostatic force) may be suitable for use in fabricating the dextran fibers of the invention. More detailed descriptions of methods of preparing the dextran fibers of the invention are provided in Example 2 below.

Other methods include compressing a dextran solution between two plates or other flat surfaces and drawing the plates or surfaces away from each other, usually repeatedly. Dextran fibers form between the two surfaces.

In some embodiments, substances other than dextran are used to form fibers for use in the hemostatic products of the invention, especially (but not exclusively) when a cotton-candy machine is employed. Examples of such substances include but are not limited to sugars such as dextrose, sucrose, etc.

The commercially available dextran that is used to produce the electrospun fibers of the invention is synthesized from sucrose by enzymes on the cell surface of certain lactic acid bacteria, the best-known being *Leuconostoc mesenteroides* and *Streptococcus mutans*. Dextran is a complex, branched glucan (a polysaccharide made of many d-glucose molecules) composed of chains of varying lengths (e.g. from 10 to 200 kilodaltons). The straight chain consists of α-1,6 glycosidic linkages between glucose molecules, while branches begin from α-1,4 linkages (and in some cases, α-1,2 and α-1,3 linkages as well).

Dextrans are commercially available in a wide range of molecular weights e.g. from about 10 kilodaltons (kDa) to about 200 kDa. Commercial preparations are mixtures of dextrans of varying molecular weights, usually in narrower weight ranges and may be provided, for example, as "low" or "high" molecular weight dextrans. For example, "Dextran 40" has an average molecular weight of 40 kDa, "Dextrans 75" has an average molecular weight of 75 kDa, etc.

In the practice of the invention, the dextrans used for electrospinning are typically in a molecular weight range of from about 10 to about 200 kDa, or from about 25 to about 200 kDa, or from about 50 to about 200 kDa, or from about 75 to 200 kDa, and usually from about 60 to 90 kDa, or from about 100 to about 200 kDa.

Further, as would be understood by those of skill in the art, the median size of the dextran molecules in a dextran preparation also has an effect in that if the median weight is high in a particular lot, less dextran may be used to form the desired amount of fibers.

In general, the conditions for electrospinning dextran are as follows: an ambient temperature of from about 60 to about 75° F., a relative humidity of from about 30% to about 40%, and typically at least about 20%. The resulting fibers are typically in the nanometer or millimeter range of cross-sectional diameter, usually from about 0.75 microns to about 1.25 microns.

The electrospun fibers are "dry" and should be protected from exposure to moisture to prevent premature dissolution. However, some water is associated with the fibers and fiber compositions can contain from about 7 to about 8% water, but must be less than about 5% when the fibers are sterilized by x-ray irradiation.

The hemostatic products of the invention are usually formed of substantially homogeneous spun dextran. The amount of dextran per hemostatic product can vary widely, depending on the size of hemostatic product that is being manufactured, with typical hemostatic product formulations using from about 5-10 grams of dextran (usually 100,000-200,000 Mr) per hemostatic product.

However, the range can be extended widely, e.g. from as low as about 0.5 grams or less (for small hemostatic products) to as high as 100 or more grams per hemostatic product, for large hemostatic products. In some embodiments of the invention, it may be helpful to use lesser amounts of dextran (e.g. about 0.1 to about 0.5 grams of dextran per hemostatic product) to concentrate the active agents that are delivered by the hemostatic product into a smaller volume.

Of more consequence is the concentration of dextran in the solution from which the fibers are spun. Generally, a solution of dextran for electrospinning will be of a concentration in the range of from about 0.1 to about 10 grams per ml of solvent, or from about 0.5 to about 5 grams per ml, and usually such a solution is at a concentration of about 1 gram per ml, ±about 0.15 mg. A preferred range would be from about 0.9 to about 1.1 grams of dextran per ml of solution that is to be spun.

Those of skill in the art will recognize that, due to the variability of molecular weight ranges in dextran preparations, and due to inherent variability from batch to batch of commercially available preparations purporting to be of a particular molecular weight range, it is typically necessary to test each batch of dextran with respect to electrospinning properties. Such tests are well within the purview of one of skill in the art, and usually involve trials of electrospinning a range of concentrations of dextran dissolved in a suitable solvent, to ascertain which concentration(s) result(s) in the most desirable fiber characteristics, e.g. stability (e.g. to heat, humidity, etc.), uniformity, cross-sectional diameter, etc.

Those of skill in the art will recognize that critical indicators of success are very obvious when trying a new batch of dextran. Too little dextran in the spinning solution results in "spitting" from the needle, whereas too much dextran results in the production of dried droplets, or failure to spin at all.

Likewise, when the humidity is too low, similar results can occur, i.e. fibers fail to form and in some cases fail to target efficiently to the ground. These characteristics can be assessed according to methods that are well known to those of skill in the art, including but not limited to visual observation, testing of fiber strength and flexibility, observation via electron microscopy, solubility testing, resistance to heat and/or irradiation, color and tendency to discoloration, etc. As would be understood by those of skill in the art, all such testing may be carried out under varying conditions of heat, humidity, etc. Formulations may also be assessed using animal testing.

The area (length and width) of a hemostatic product of the invention can vary widely and can be adjusted by adjusting spinning parameters. In addition, the mats of dextran fibers can be cut to a desired size after spinning Generally, a hemostatic product will be from about 0.5 centimeters or less to about 30 centimeters or more in length and/or width, but larger or smaller sizes are also contemplated.

The height or thickness of the hemostatic product can likewise vary considerably depending on the intended use of the hemostatic product. In certain embodiments, the hemostatic product has a thickness of between about 1 millimeter and about 5 centimeters.

The thickness of the hemostatic product (which is related to the volume) may impact the rate of dissolution of the dextran upon contact with liquid. For example, a thin hemostatic product (e.g. about 2 millimeters), will dissolve more rapidly than a hemostatic product that is thicker, providing the loft of the fibers is comparable.

In most embodiments, dissolution of the dextran fibers is extremely rapid, e.g. about 5 minutes or less after exposure to liquid, or about 4 minutes or less, about 3 minutes or less, or about 2 minutes or less, or about 1 minute or less, e.g. the hemostatic product typically takes only a few seconds to dissolve (e.g. from about 1 to about 20 seconds to dissolve.

This rapid dissolution may be referred to herein as "instantaneous" or "immediate" dissolution. Compression of an electrospun dextran mat may be used to modulate the rate of dissolution, with greater levels of compression inversely impacting the rate, i.e. generally, the greater the degree of compression, the slower the rate of dissolution. The rapid rate of dissolution is advantageous, particularly when delivering biologically active agents (e.g. hemostatic agents) to a site of action such as a wound. Rapid dissolution of the carrier dextran fibers provides extremely rapid delivery of the hemostatic agents to the wound upon deployment of the hemostatic product.

Those of skill in the art will recognize that a plethora of liquid solvents exist in which it is possible to dissolve dextran. However, superior results for electrospinning dextran are generally achieved when the solvent is water, especially deionized or distilled or deionized, distilled (ddH$_2$O) or other forms of relatively pure water. In addition, there is far less environmental impact associated with the use of water.

It has been found that, generally, high concentrations of salt in the solvent should be avoided. Whereas salt is often used to facilitate the spinning of some electrospun polymers, this is not the case for dextran. The concentration of salts in the spinning solution should be kept at a minimum to successfully form dextran fibers.

The one or more active agents that are associated with the dextran fibers of the hemostatic product may be any active agent that it is desirable or advantageous to deliver to the site where the electrospun dextran fiber device is to be used or applied. In one embodiment of the invention, the electrospun dextran fiber device is a hemostatic product and is used to deliver beneficial agents, for example, to a wound.

Such wounds include wounds and breaches of body or tissue integrity that occur as a result of trauma (e.g. accidental trauma, trauma resulting from conflicts such as gunshot wounds, knives, etc.), as well as wounds which are purposefully incurred, such as surgical incisions, body piercings, etc.

Usually the agents are bioactive agents that have a beneficial or therapeutic effect at the wound site. In one embodiment, the site is a bleeding wound at which it is desired to form a blood clot to stop or slow the bleeding. In this embodiment, the therapeutic substances of interest may include, for example, thrombin and fibrinogen, although other agents active in promoting hemostasis, including but not limited to capscian, may also be included.

In addition, electrospun or non-electrospun collagen, agents that absorb water, various dry salts that would tend to absorb fluids when placed in contact with e.g. blood; engineered thrombin or thrombin mimics; engineered fibrinogen; agents that cause vasospasm (e.g. ADP, 5-hydroxytryptamine, 5-HT and thromboxane, (TXA-2) to help contract and seal a bleeding vessel, etc. may also be included.

In addition, other components of the clotting cascade may be added to the hemostatic product, for example: tissue factors that are normally only expressed on the surface of damaged cells and which start the normal clotting cascade; serotonin which enhances platelet clumping and promotes vessel constriction; and other agents that are used to replace missing components of the clotting cascade in hemophilia, for example, factor 7 (which activates the so called external extrinsic coagulation cascade) and crude extracts of platelets.

Figure 10:
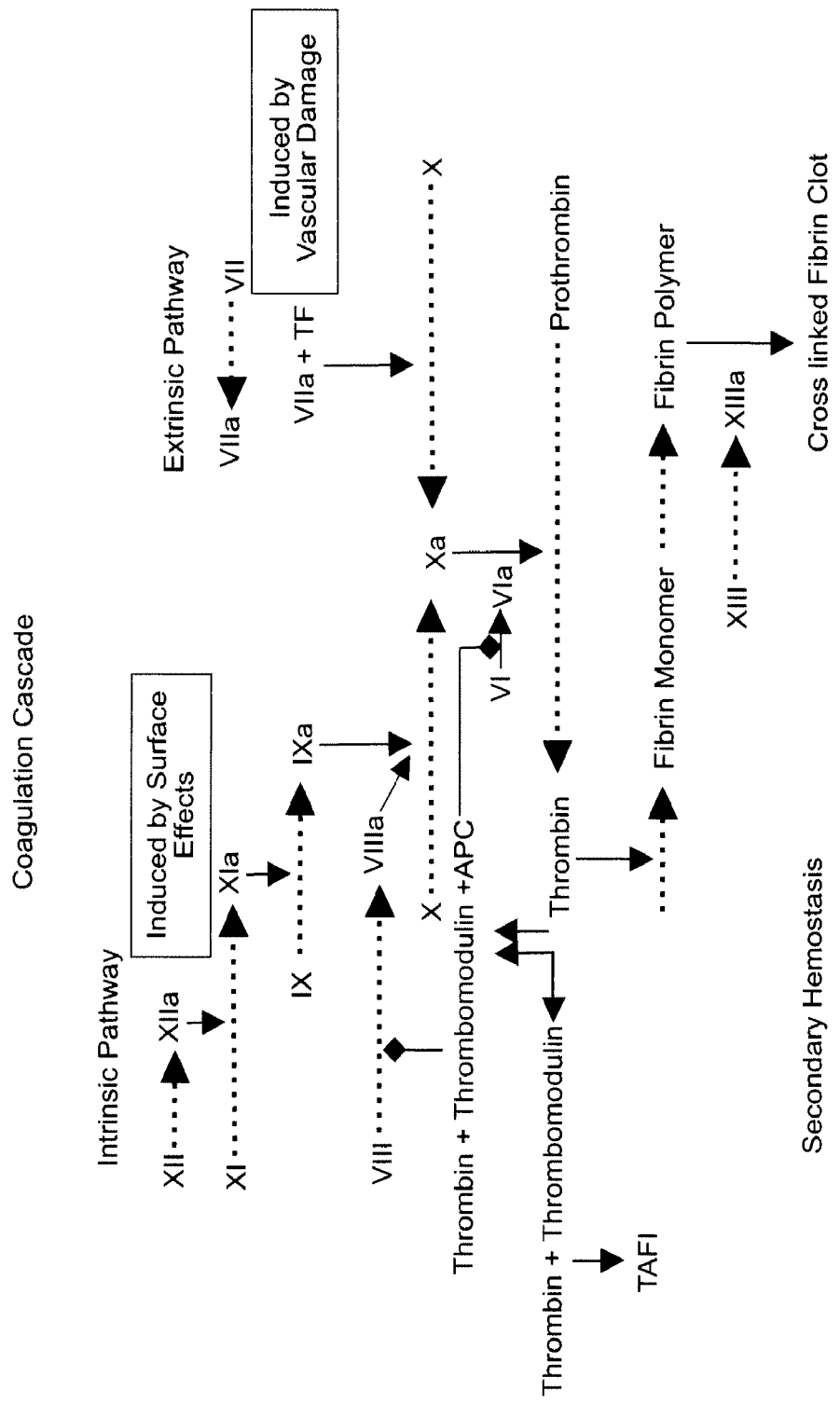
FIG. 10. Schematic of the coagulation cascade.

These agents essentially work to "jump start" clotting by initiating the cascade further down the reaction network, as illustrated in FIG. 10. In FIG. 10, the various factors (and their alternative nomenclature and/or characteristics and/or activities) are as follows:

Factor VII (Proconvertin): serine protease, Vitamin K dependent synthesis in the liver;

Factor VIII: Glycoprotein binds vWF, produced by endothelium and liver;

Factor IX (Christmas-Eve Factor): serine protease;

Factor X (Stuart-Prowler Factor, Clotting Factor X): serine endopeptidase, converts prothrombin to thrombin; and Factor XI (Plasma thromboplastin antecedent): serine protease, plasma protein;

Factor XII (Hageman factor): serine protease, plasma protein binds collagen;

Factor XIII (Fibrin stabilizing Enzyme): stabilizes fibrin polymer. plasma protein, also present in platelets and monocyte linage.

In FIG. 10, italic pathways denote inhibition and the central role of thrombin in the activation of coagulation and inactivation of coagulation processes is shown, where:

VI=Cofactor for Xa in the conversion of prothrombin to thrombin;

APC=Activated Protein C, an extracellular signal molecule, inhibits FVI (equivalent to FVa, a cofactor of XA in the conversion of prothrombin to thrombin) and FVIIIa through a proteolytic event; and TAFI=Thrombin Activatable Fibrinolysis Inhibitor, an inhibitor of clot lysis.

In addition, active agents that function to promote late stages of wound healing may also be included to, for example, facilitate cell migration and remodeling. The incorporation of collagen is an example of such an active agent.

One or more of any of these active agents may be used in the practice of the present invention. The therapeutic agents must be amenable to drying and are associated with the other components of the hemostatic product in the dry state, since liquid may negatively affect at least one of the components used in the hemostatic product. For example, the active agents may be desiccated or lyophilized, or water may be removed by some other means.

Generally, the amount of water that is present in the substances when they are associated with the electrospun dextran fibers is less than about 5%, and preferably less that about 2%. These substances retain full or partial activity when rehydrated, e.g. in blood. Generally therapeutic substances associated with the devices of the invention retain, upon contact with liquid, at least about 25%, or about 50%, or even about 75 to 100% of their activity before drying or desiccation, as compared to standard preparations of the substance using standard assays that are known to those of skill in the art.

In some embodiments, thrombin or fibrinogen, or both, are associated with the hemostatic product. In some embodiments, the thrombin and fibrinogen are salmon thrombin and fibrinogen. Advantages of using salmon as a source of these materials include but are not limited to the lack of concern about transmission of etiologic agents (e.g. viruses) that may occur when human and other mammalian sources of thrombin or fibrinogen (e.g. bovine) are used.

Salmon thrombin and fibrinogen are highly efficacious and have no deleterious side effects, when used in the pig model, which is a recognized animal model that is considered to be indicative of results in humans.

The quantity of fibrinogen added to the hemostatic product is generally in the range of from about 10 milligrams to about 3 grams. In certain embodiments, the amount of fibrinogen in each of the hemostatic products is between about 20 milligrams to about 1 gram.

The quantity of thrombin added to each of the hemostatic products is generally between about 10 and 10,000 NIH Units. In certain embodiments, the amount of thrombin in each of the hemostatic products is between about 20 and 6,000 NIH Units.

In some embodiments, the therapeutic agents may themselves be electrospun. For example, the therapeutic agents are dissolved in and spun from a solution. In some embodiments, the therapeutic agents may be electrospun into fibers. In other embodiments, the active agents may be electrospun into other forms such as droplets, beads, etc.

In some applications, active agents such as thrombin may be electrosprayed with sucrose to form sugar droplets, which tends to stabilize thrombin and can also "trap" other substances of interest for delivery to the hemostatic product.

For thrombin and fibrinogen, in most embodiments, these (or other) active agents are in a finely dispersed dry, particulate or granular form e.g. as a fine powder or dust, as electrospinning may tend to decrease their activity. In other words, the active agents are not electrospun either by themselves.

The provision of the substances in the form of a fine powder provides a large surface area of contact for dissolution when the materials come into contact with fluid. Generally, such particles will have average diameters of between about 1 and 10,000 microns, and, in certain embodiments, between about 10 and 1,000 microns.

Such dry solid particles may be formed by any of several means, including but not limited to grinding, pulverizing, crushing, etc. However, those of skill in the art will recognize that other forms of these active agents may also be included in the hemostatic product, e.g. flakes, films, sheets, strings, etc. Further, in some embodiments, thrombin and fibrinogen are in the form of electrospun droplets when associated with an excipient or carrier.

Association of substances of interest with the excipient or carrier may be accomplished by any of many suitable techniques that are known to those of skill in the art, and will depend in part on the precise form of the substance and the means at hand. For example, for powdered, particulate thrombin and fibrinogen, association may be carried out by sprinkling, shaking, blowing, etc. the agents onto a layer of the excipient or carrier.

Depending on the density of the fiber mat, the substances of interest may become relatively evenly dispersed throughout the woven mat of fibers or may be largely confined to the topmost section of the fiber mat. If no backing is present, the latter embodiment is preferable, to prevent the particulate substance of interest from falling through and out of the mat.

The density of the fibrous mat can be adjusted (e.g. increased), for example, by adjusting its thickness and/or by compressing the mat under pressure so that the fibers are closer together. Other techniques for association also exist, e.g. the placement of dry but liquid soluble sheets or strips of material onto or between layers of a carrier, electrospinning the added materials as a discrete layer or in discrete layers, etc., and any such technique may be employed.

The techniques for assembling the hemostatic products of the invention may be carried out manually or may be mechanized, or a combination of manual manipulation and mechanization may be used. For thrombin in particular, 5,000 NIH Units of thrombin is a relatively small volume of powder. Therefore, inert carriers or bulking agents such as dextrose may be added to insure more complete dispersal of active agents in the hemostatic product.

The association of substances of interest with the excipient may be carried out according to many different arrangements. For example, a first layer of excipient may be formed, and one or more of the substances may be associated with the first layer. Then another second layer of excipient may be formed on top of the substance(s) of interest, and the same or other substances of interest may be associated with the second layer, and so on.

A final or outermost layer of excipient may be added to prevent the dislodgement of substances of interest from the layer(s) below. The number of layers of excipient that are used in a hemostatic product of the invention may vary widely, from as few as 1-2 to as many as several dozen, or even several hundred, depending on the desired characteristics of the hemostatic product.

Typically, a hemostatic product will contain 1-2 layers. In other embodiments the hemostatic product may include between 2-20 layers. The very slight amount of moisture that is present in a prepared hemostatic product may help to trap and retain the thrombin and fibrinogen on the surface of the hemostatic product.

In some embodiments of the invention, the hemostatic products also include one or more support structures or support materials incorporated therein. For example, a backing may be incorporated into the hemostatic product.

The support material may be formed from various electrospun materials such as polyglycolic acid (PGA), polylactic acid (PLA), and their copolymers (PLGAs); charged nylon, etc. In one embodiment, the support material is compressed electrospun dextran fibers. By "compressed electrospun dextran fibers" we mean that electrospun dextran fibers are compressed together under pressure.

Compression of electrospun dextran fibers is carried out, for example, under pressure between two plates (e.g. a vice), and can compress a mat of fibers with a height (thickness) of about 3 inches to a sheet with a height of about 0.5 inches or even less (e.g. about 0.1 to about 0.4 inches). In some embodiments, the electrospun dextran fibers are electrospun directly onto a previously electrospun support material, while in other embodiments, the support material and the electrospun dextran fibers are associated after electrospinning of each, e.g. by joining of one or more layers of each.

In other embodiments, the support material is not an electrospun material but is some other (usually lightweight) material. Examples of such materials include but are not limited to gauze; various plastics; hydrogels and other absorbent materials that can facilitate absorption of blood and therefore clot formation; etc.

The support material may or may not be soluble in liquid, or may be slowly soluble in liquid, and may or may not be permeable to liquid. Slowly soluble materials include those from which absorbable or dissolving (biodegradable) stitches or sutures are formed, included PGA, polylactic and caprolactone polymers.

In certain embodiments, the support material may dissolve relatively quickly such as less than about 1 hour. In other embodiments, the support material may dissolve within from about 10 days to 8 weeks. In either case, the support material provides the advantage of not having to remove the hemostatic product and risk disrupting the clot.

However, in any case, the support material should not interfere with the immediate dissolution of the excipients and delivery of the active agents associated therewith into the liquid that dissolves the excipients. Thus, the support material might be only on one side of the electrospun dextran fiber device, so that when the device is, for example, a hemostatic product, and is applied to a wound, the hemostatic product is oriented so that the excipients come into direct contact with the blood in the wound bed and the support material does not, i.e. the support material is the "top" or outermost surface of the hemostatic product when placed on the wound.

Figure 4A:
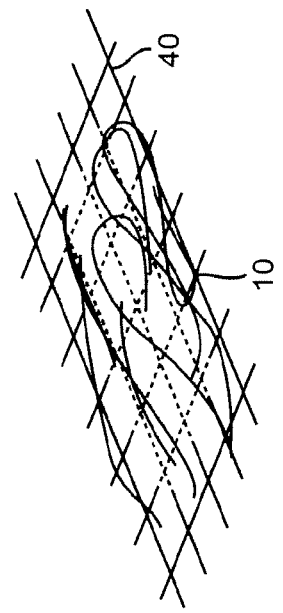
FIG. 4A-E. Schematic representations of exemplary hemostatic products formed form electrospun dextran fibers. A, hemostatic product with non-permeable support material as a backing; B, hemostatic product with net-like support material; C, hemostatic product with non-permeable backing and a net-like support material holding the electrospun fibers in place on the backing; D, hemostatic product for delivery of therapeutics to a deep wound; E, alternative embodiment of a hemostatic product for delivery of therapeutics to a deep wound.

This embodiment is illustrated, for example, in FIG. 4A, in which electrospun dextran fibers 10 are shown as deposited onto non-porous, liquid impermeable support material 20. When applied to a wound, excipient 10 would face downward into the wound, and non-porous support material 20 would face away from the wound.

This arrangement could provide an advantage in that pressure could be applied to the wound through the support material, to facilitate the stoppage of bleeding. Alternatively, the support material may contain pores, openings or spaces that allow liquid to access the excipients in the hemostatic product even when the support material is present. For example, the support material may be a net or web of material that is insoluble (or slowly soluble) but that permits liquid to freely access the excipients and associated substances of interest.

Figure 4B:
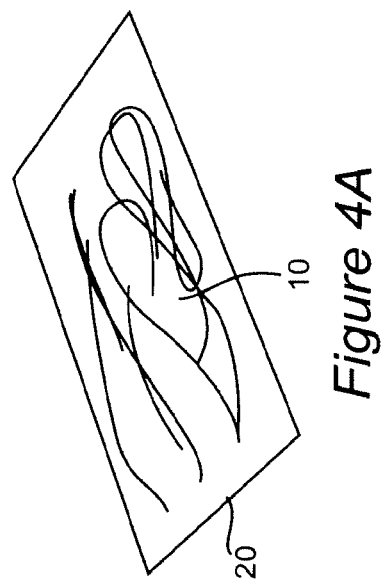

This embodiment is illustrated schematically in FIG. 4B, which shows electrospun dextran fibers 10 deposited on (or possibly under, or on and under, or woven throughout) netting 40, which is shown partially in phantom where covered by electrospun dextran fibers 10. In yet other embodiments, both a "backing" or "top" support material and a second web-like support material may be present in the devise.

Figure 4C:
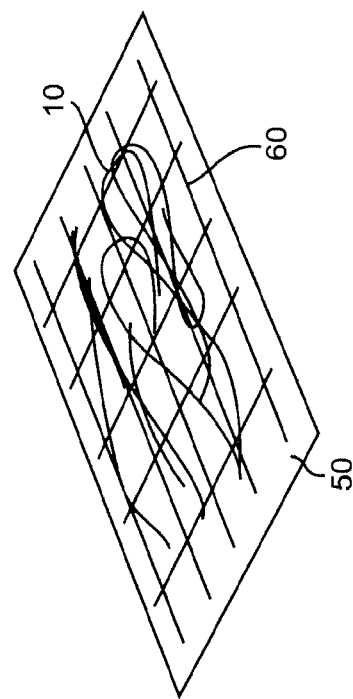

This embodiment is illustrated schematically in FIG. 4C, which shows electrospun dextran fibers 10 deposited on non-porous support material 50 and overlaid with net-like material 60, i.e. electrospun dextran fibers 10 are "sandwiched" between non-porous support material 50 and net-like material 60.

One of skill in the art will be able to envision many other combinations and shapes of excipient layers and support materials that would provide advantages in particular scenarios. For example, excipients might be wrapped or wound around an elongated support such as a filament or string, or wrapped around a particular form with the shape of a cavity in which the hemostatic product is likely to be placed, such as a bullet hole, etc.

In one such embodiment, the fibrinogen is provided in a powder and that powder is dispensed on the surface of one of the layers of the hemostatic product. In other embodiments, the fibrinogen is mixed with thrombin and then the fibrinogen-thrombin mixture is spread on one of the layers in the hemostatic product. The fibrinogen may be provided on the surface of each hemostatic product at a concentration of up to about 10 grams per hemostatic product.

In another embodiment of the invention that is directed to fabricating the hemostatic product, dextran is mixed with water until a substantially homogeneous mixture is prepared. The dextran may be provided in a powder having a relatively fine particle granulation. The dextran and water may be selected to have a relatively high purity such as is typically used in medical applications. An example of one such suitable water is distilled water.

In one such configuration, there are between about 3 grams and about 9 grams of dextran with about 6 milliliters of water. In other embodiments, there are about 6 grams of dextran is mixed with about 6 milliliters of water. A person of skill in the art will appreciate that a variety of techniques may be used to mix together the dextran and water to produce the substantially homogeneous mixture from dextran and water. A non-limiting example of a technique that may be used to mix together the dextran and water is electrospinning.

The duration of mixing that is needed to prepare the substantially homogeneous mixture of dextran and water may depend on a variety of factors such as the type of equipment that is used to perform the mixing. In certain configurations, this mixing is performed for greater than about 30 minutes. The mixing may be performed at a temperature of between about 40° F. and about 70° F.

Next, thrombin is mixed with the dextran-water mixture. The thrombin is added to the dextran-water mixture to provide the hemostatic product therefrom with a concentration of thrombin that is between about 20 and 6,000 NIH Units.

Thrombin may be provided in a powder having a relatively fine particle granulation. The thrombin may be selected to have a relatively high purity such as is typically used in medical applications.

Similar to the process used to prepare the dextran-water mixture, electrospinning may be used when mixing the thrombin with the dextran-water mixture. The mixing of the thrombin with the dextran-water mixture may be performed at a temperature of between about 40° F. and about 70° F.

The duration of mixing that is needed to prepare the substantially homogeneous mixture of thrombin, dextran and water may depend on a variety of factors such as the type of equipment that is used to perform the mixing. In certain configurations, the mixing is performed for between about 10 and 30 minutes. In other configurations, the mixing is performed for about 1 hour.

Once the mixing is completed, the mixture is introduced into an electrospinning machine. The electrospinning machine is configured to produce a sheet having a width of up to about 1 meter. However, shorter widths may also be used depending on the desired dimensions for the hemostatic product.

A release sheet is placed beneath the electrospinning machine onto which the fibers are placed. The release sheet provides support for the fibers during the processing and cutting. The release sheet should be selected to not interact with the components being used in the fabricating the hemostatic product. The release sheet may be configured to be separated from the product after the cutting and/or other processing is completed.

Because of factors such as challenges associated with incorporating the fibrinogen with the other components utilized in forming the hemostatic product, the fibrinogen may be provided on a surface of one of the layers in the hemostatic product as opposed to being incorporated into one or more of the layers.

The crux of the problem at the site of a penetrating injury is that the wounded tissue is relatively inaccessible. For example, for a bullet wound (e.g. in the leg or thigh) bleeding does not occur as much at the surface but deeper within the tissue, within a cavity formed by the bullet, where it cannot be easily treated by a hemostatic product that is simply spread over the external site of the injury (e.g. the point of entry of the bullet, knife, shrapnel, sword, bayonet, etc., or other cause of injury).

This aspect of the invention solves the problems associated with penetrating injuries, which can cause extensive bleeding in the deep tissues, and takes advantage of the highly soluble nature of the dextran hemostatic product. A complicating factor in this type of injury concerns the ability to deliver hemostatic materials that are highly soluble to such a site.

There may be bleeding and other fluids evident at the entry site of the wound and the application of a hemostatic product to this superficial site may result in the complete dissolution of the hemostatic product at the surface-without the delivery of the active materials to the underlying source of the bleeding within the wound cavity. The invention circumvents this occurrence by providing delivery of active agents deep into the wound. Prior art hemostatic products have failed to adequately address this problem.

The present invention solves this problem by providing a hemostatic product, the shape and application of that can be adapted to use with such wounds. For example, an elongated cylindrical "cigar-shaped" hemostatic product that contains thrombin and fibrinogen, and which may contain support material, is provided.

The hemostatic product may be stored within a protective covering or packaging or tube. This tube protects the hemostatic product from the ambient environment. Both the hemostatic product and the tube are preferably sterile. These components may be further enclosed in an outer wrapper of e.g. paper, polymer, blister pack, similar to that used for disposable syringes, to prevent loss of sterility.

When used, the outer wrapping is torn open and the sterile tube containing the hemostatic product is accessed. In some embodiments, one end of the tube is removed and placed over the outermost accessible portion of the injury. The tube may also comprise a "plunger" or similar means which enables the user to expel the hemostatic product from the tube and into the wound, in effect "injecting" the hemostatic product into the wound.

Means such as those that are used for the vaginal delivery of, for example, tampons, (i.e. a "cylinder within a cylinder") may be employed, or a syringe-like means of delivery may be used. The hemostatic product can thereby be introduced deep into the tissue along the wound track and the therapeutic agents in the hemostatic product are delivered to where they are most needed, i.e. to the interior of the wound.

In other embodiments, a plunger per se is not included, but the tube is fashioned so that both ends can be opened, and the hemostatic can be pushed into the wound from one open end by exerting pressure on the opposite open end of the tube using any object that fits at least partially into the tube, sufficiently to push the hemostatic product out of the tube and into the wound. Examples of such objects include a finger and a stick.

Such an object may be included with the hemostatic product of the invention. Those of skill in the art will recognize that, due to the relatively high malleability of some configurations, this embodiment of the hemostatic product may include support material around or within the hemostatic product (e.g. biologically compatible netting, rod, etc. that will disintegrate via biodegradation) to render the hemostatic product more robust and less flexible as it is shunted down into the wound.

Further, the outermost end of the hemostatic product, that end on which pressure is exerted (e.g. with a plunger) to expel the hemostatic product from the tube into the wound, may be reinforced with support material so that the plunger or other object used to push on the hemostatic product can deliver sufficient force to remove the hemostatic product from the tube.

Figure 4D:
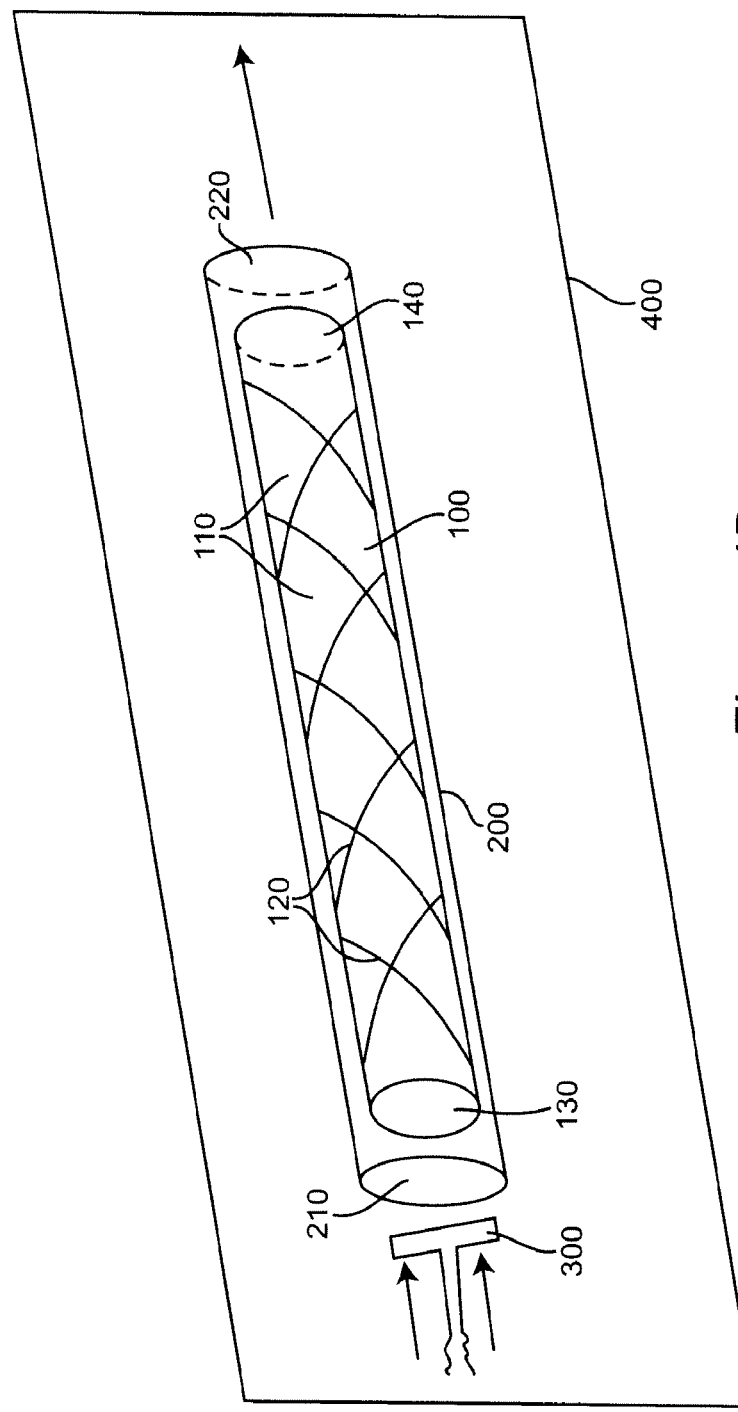

An exemplary schematic depiction of this embodiment of the invention is provided in FIG. 4D, where hemostatic product 100, comprised of spun dextran fibers 110 and (optional) support material 120, and having a first end 130 and second end 140 is illustrated as enclosed within tube 200.

Hemostatic product 100 is enclosed within tube 200 but is not shown in phantom for the sake of clarity. Tube 200 has openings 210 and 220, both of which may be capped prior to use (caps not shown) or may be left open, especially if the entire apparatus is packaged in sterile packaging 400. Sterile packaging 400 is removed or breached to provide access the apparatus prior to use. To use the apparatus, openings 210 and 220 of the tube must be open.

Figure 4E:
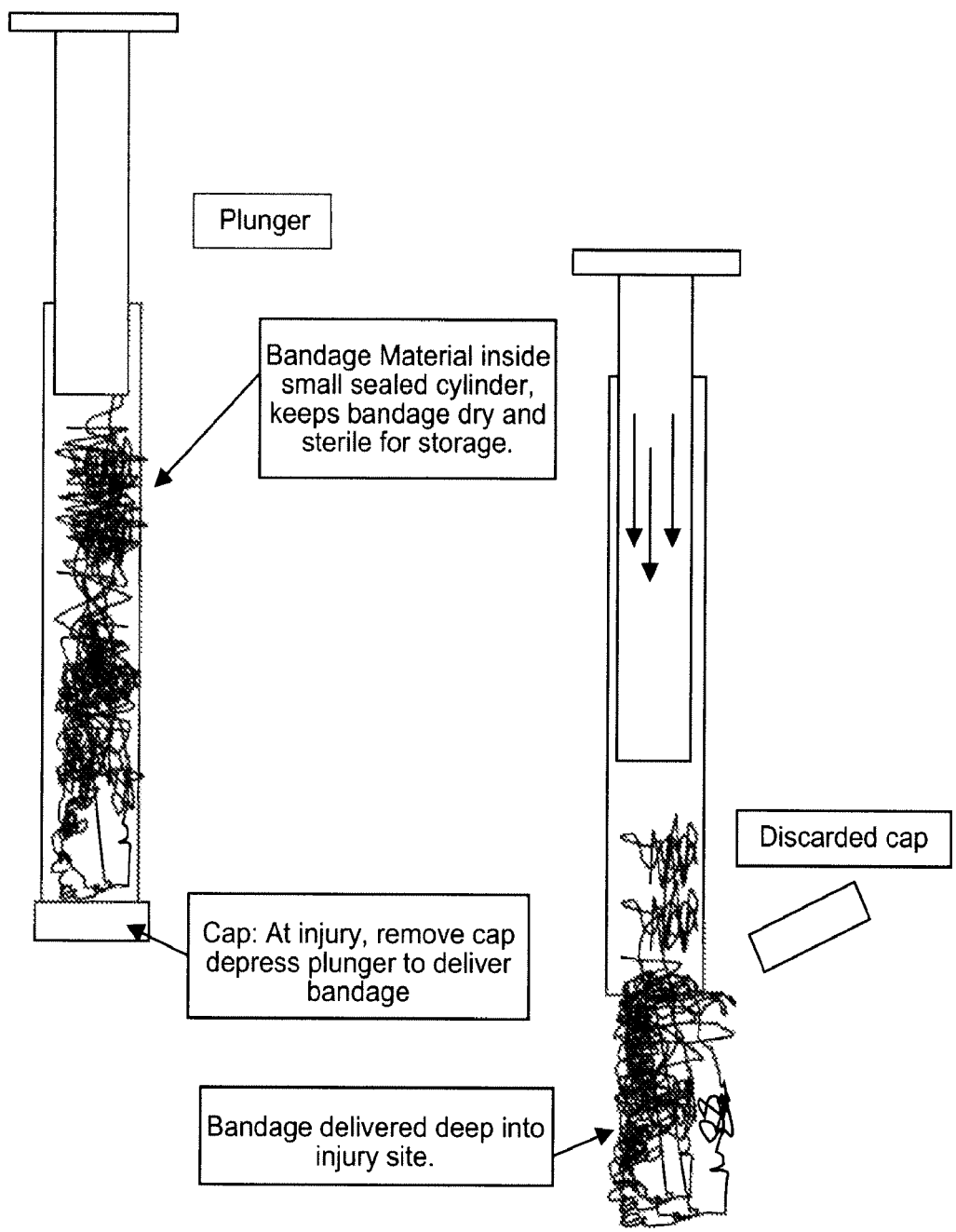
Figure 5A:
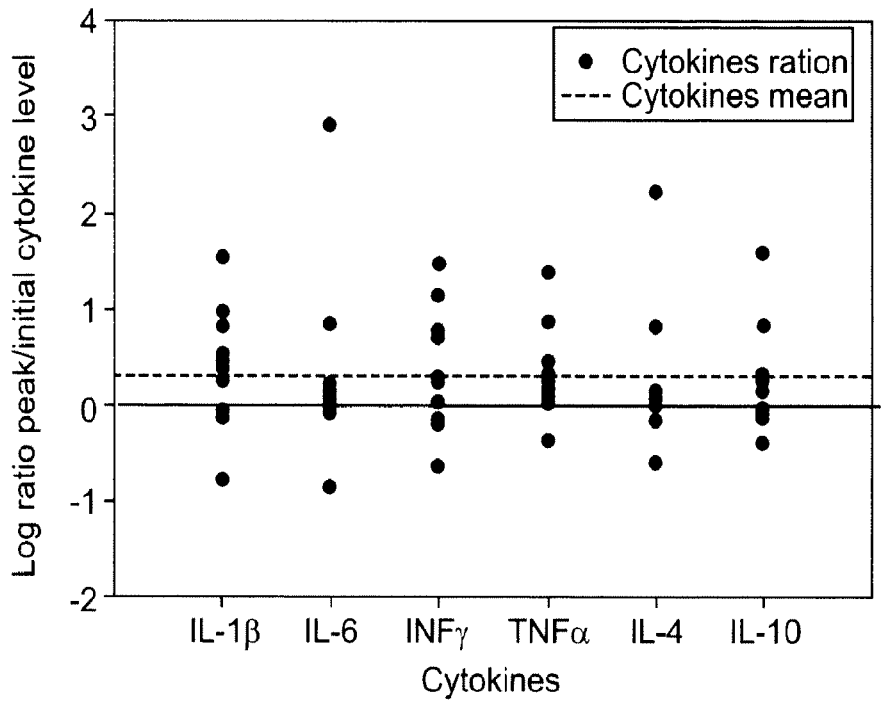
FIGS. 5A and B. Changes in cytokine levels in animals exposed to the salmon fibrinogen/thrombin hemostatic product. (A) Levels of IL-1$\beta$, IL-6, TNF-$\alpha$, IFN-$\gamma$, IL-4 and IL-10 are shown as the log ratio of the cytokine level determined in blood drawn at the initial surgery to implant the vascular port compared to peak levels following exposure. Changes were seen in both pro-inflammatory responses (IL-1$\beta$, IL-6, TNF-$\alpha$, IFN-$\gamma$) and humoral responses (IL-4 and IL-10). (B) Changes in the cytokines within an individual animal show that initial exposure (first arrow) and the subsequent intravenous infusion of proteins (second arrow) elicited a response that could be detected in samples taken at the next blood draw.
Figure 5B:
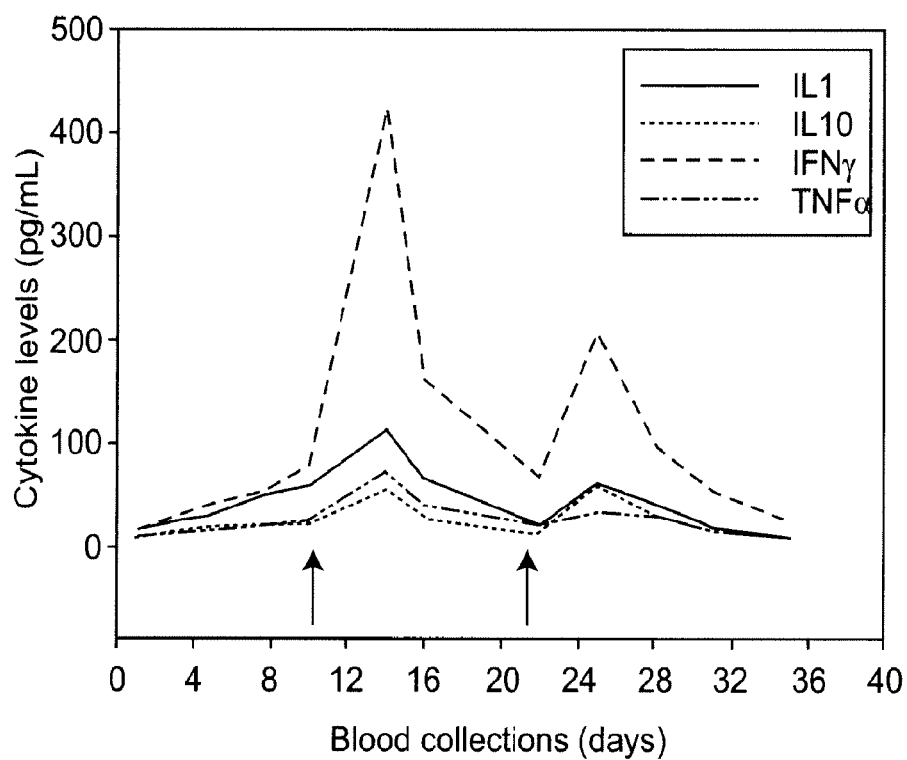
Figure 7A:
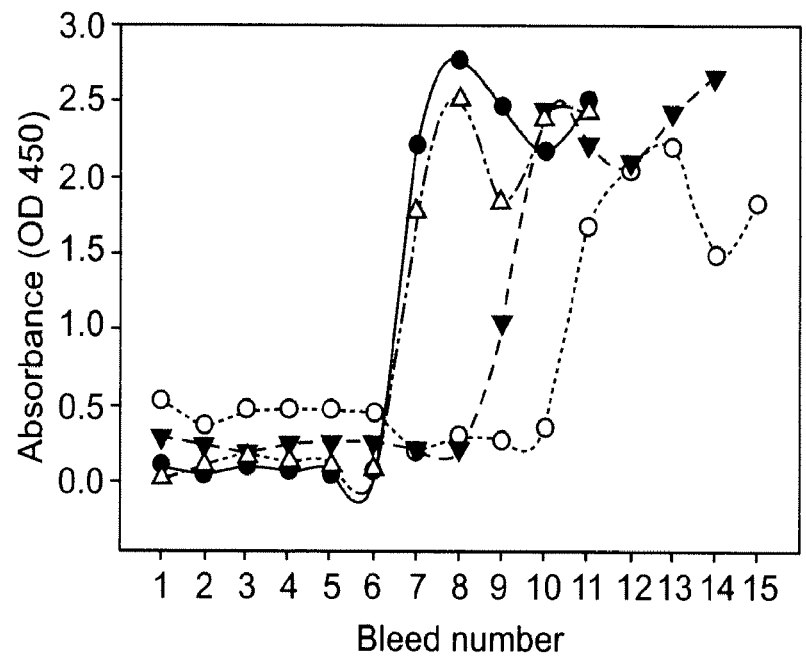
FIG. 7A-D. Time course of antibody development in animals exposed to salmon thrombin/fibrinogen hemostatic products through the dermal patch protocol. ELISAs were performed using anti-IgG reagents. The following antigens were used as the targets in the ELISAs: (A) salmon fibrinogen, (B) salmon thrombin, (C) human fibrinogen and (D) human thrombin. The increases in absorbance observed at the later samples panels A, B, C occurred following intravenous infusion of salmon proteins. Each curve represents data from a different animal.
Figure 7B:
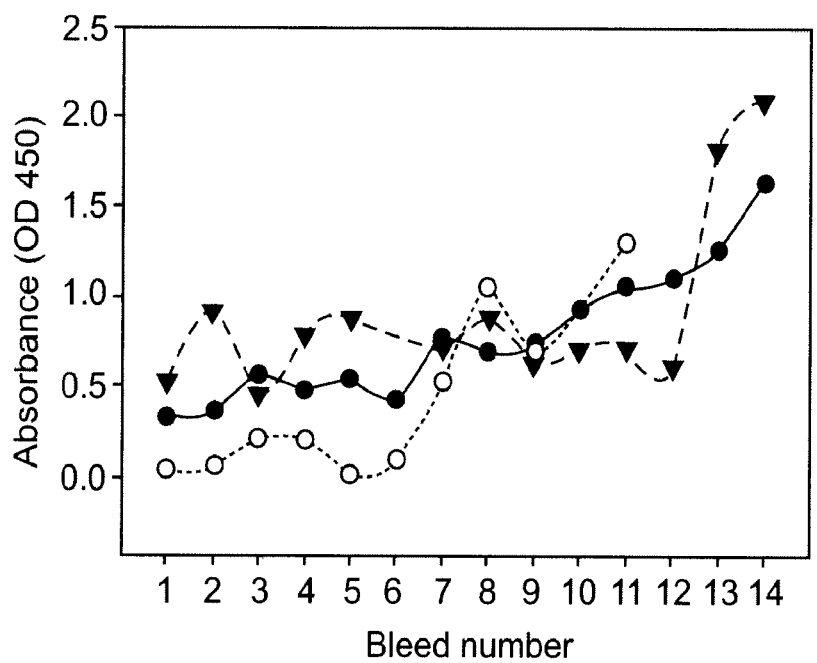
Figure 7C:
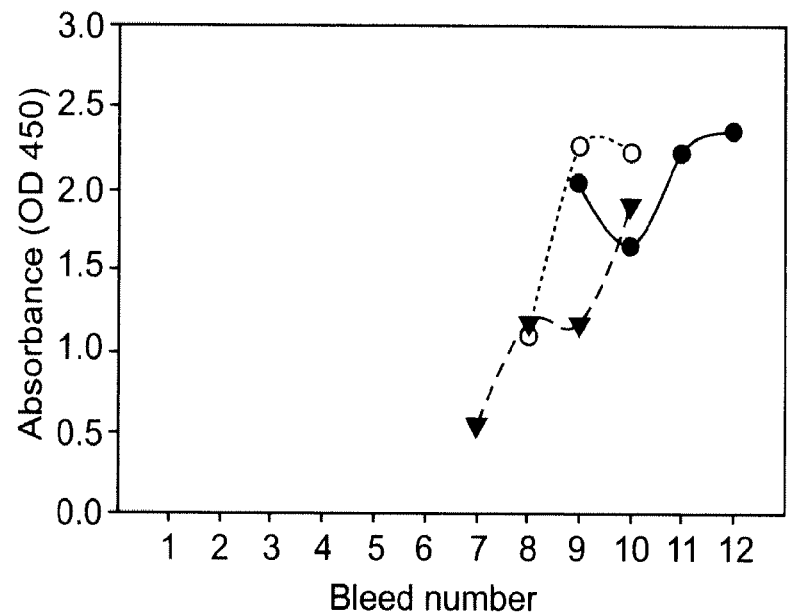
Figure 7D:
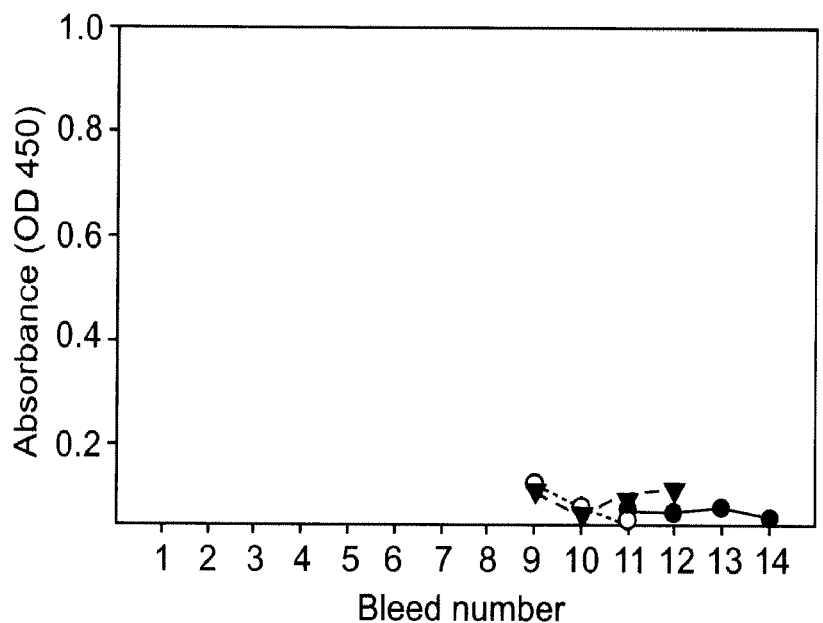
Figure 8A:
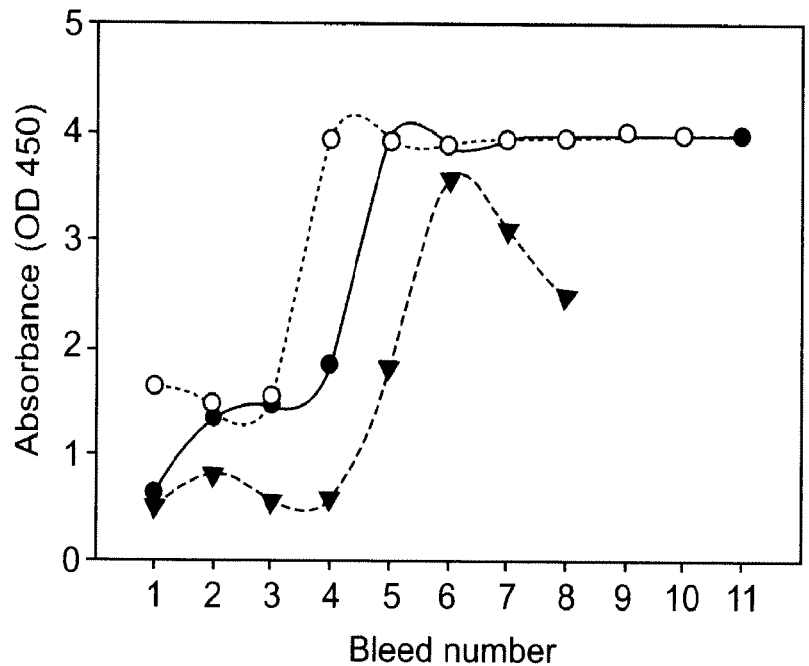
FIG. 8A-D. Time course of antibody development in animals exposed to salmon thrombin/fibrinogen hemostatic products through the abdominal patch protocol. ELISAs were performed using anti-IgG reagents. The following antigens were used as the targets in the ELISAs: (A) salmon fibrinogen, (B) salmon thrombin, (C) human fibrinogen and (D) human thrombin.
Figure 8B:
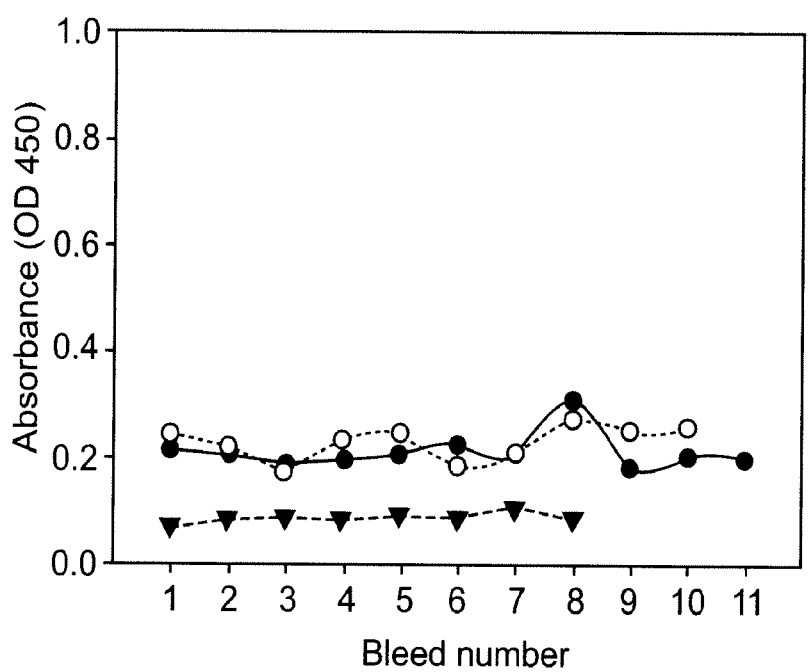
Figure 8C:
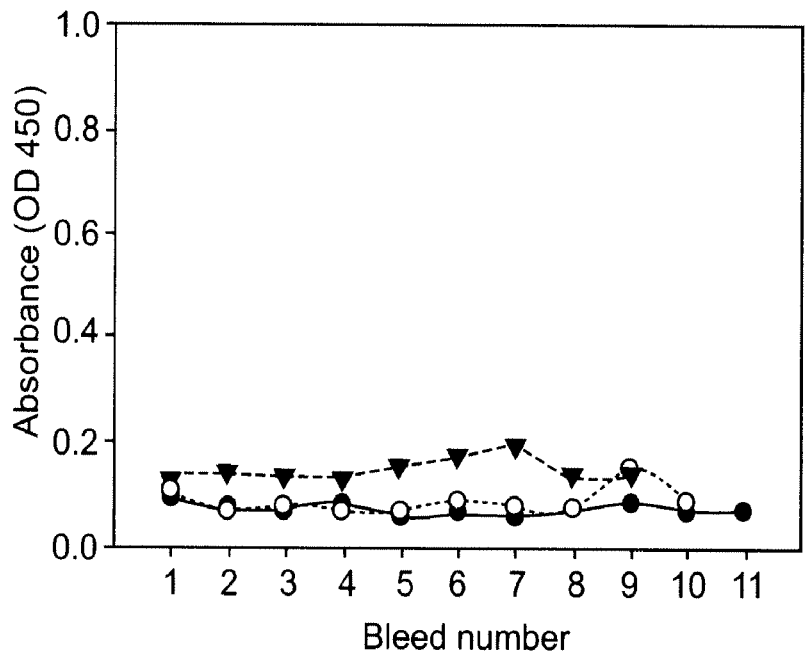
Figure 8D:
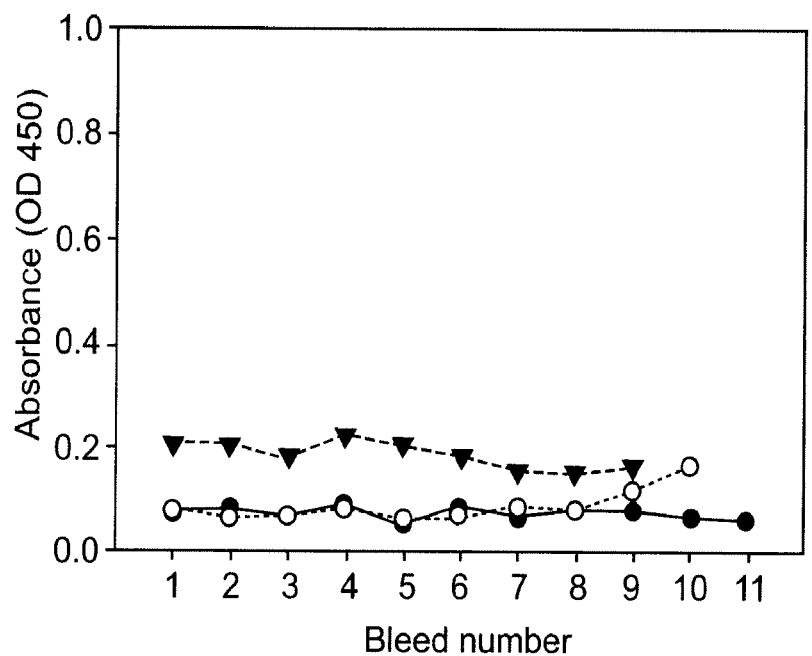
Figure 9A:
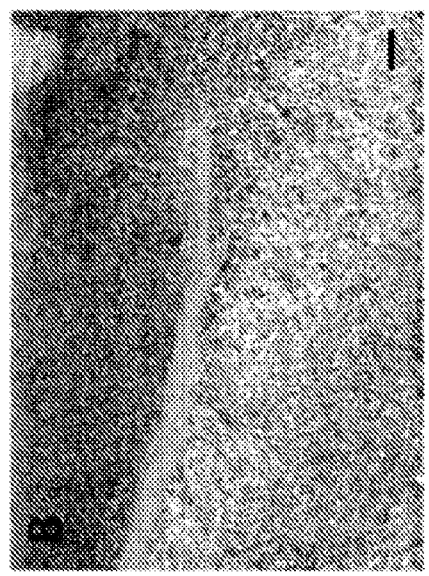
FIG. 9A-D. Progression of dermal healing following full-thickness wound. Images from samples taken at 7 days from control (A) and salmon hemostatic product-treated (B) injuries show a fibrinonecrotic coagulum filling the wound defect (*) and an epithelial cell projection towards wound center in both cases as wound healing progresses following initial clotting. (H&E staining, bars=100 um). Samples taken at 28 days from control (C) and salmon hemostatic product-treated (D) injuries show complete re-epithelialization by a hyperplastic and hyperkeratotic epidermis. (H & E staining, bars=100 um).
Figure 9B:
Figure 9C:
Figure 9D:

To deliver hemostatic product 10 to a penetrating wound, an object such as plunger 300 in inserted into end 210 of the tube. Pressure is exerted on hemostatic product 100 as plunger 300 contacts device end 130, and hemostatic product 100 is consequently pushed out of tube 200 via opening 220 (in the direction indicated by the arrows) and into the penetrating wound (not shown). A second schematic representation of such a hemostatic product is provided in FIG. 4E.

In this depiction, support material is not included and the dry, sterile hemostatic product material (e.g. dextran fibers) with associated therapeutic agents is located or positioned within a small, sealed cylinder with a cap at one end and a plunger at the other. Upon deployment, the cap is discarded, the open end of the cylinder is placed over the mouth of the wound and may be inserted into the wound, and the plunger is depressed, displacing or injecting the hemostatic product material deeply into the wound.

Similar designs may be used to deliver the hemostatic product to orifices or channels such as the nasal passages, the ear canal, the vagina, the anus, into blood vessels, etc. The components that are used in such an application will be formed into a shape that is on the order of about 1 to about 6 inches in length, and from about ¼ inch to 1 inch in diameter, i.e. the dimensions of the hemostatic product will be suitable for insertion through the external opening and deep into an orifice or a wound cavity.

All such arrangements, shapes, and embodiments of carrier layers and support materials as described herein are intended to be encompassed by the invention.

The hemostatic product may be sterilized prior to use, generally by using electromagnetic radiation, for example, X-rays, gamma rays, ultraviolet light, etc. If thrombin is included in the hemostatic product, it may be desirable to reduce the moisture content of the hemostatic product (e.g. a bandage or gauze) to less than about 5%, to preserve thrombin activity during sterilization.

This moisture content reduction can be achieved by drying the fabricated hemostatic product, e.g., under a vacuum, or by using a fabrication method that reduces moisture content from the beginning. Typically, the hemostatic products are sterilized using X-rays in a dose of between about 5 and 25 kilograys (kGray). Any method that does not destroy the carrier or the activity of substances associated with the fibers may be used to sterilize the hemostatic products of the invention.

When the hemostatic product is a bandage, the substances of interest that are associated with the fibers of the hemostatic product may include thrombin and fibrinogen, and the hemostatic product may be used to staunch bleeding. However, the range of active ingredients may vary with the specific application of the hemostatic product.

For example, hemostatic products comprised of only thrombin might be used for small injuries or in combination with other interventions. In addition, other therapeutically beneficial substances may also be associated with the hemostatic product, including but not limited to: antibiotics, medicaments that alleviate pain, growth factors, bone morphogenic protein, vasoactive materials (e.g. substances that cause vasospasms), steroids to reduce inflammation and combinations thereof.

In other embodiments, the devices of the invention do not contain agents that promote clotting. Those of skill in the art will recognize that the devices of the invention are highly suitable for delivering many substances of interest to a desired liquid environment or location. For example, the devices may be designed for delivery of therapeutic or beneficial substances to any moist environment of the body, where there is sufficient liquid to dissolve the electrospun dextran fibers and release the active substance, and where dissolved dextran is not problematic.

Examples include but are not limited to oral, nasal, tracheal, anal, lung, and vaginal delivery of substances such as anti-microbial agents, analgesic agents, nutritional agents, etc. Oral applications include the delivery of substances useful for dental treatments, e.g. antibiotics, pain medications, whitening agents, etc. Examples of therapeutic or beneficial substances that can be used in conjunction with the devices include antibiotics, medicaments that alleviate pain, growth factors, bone morphogenic proteins, vasoactive materials (e.g. substances that cause vasospasms), inflammation reduction steroids and combinations thereof.

However, in some embodiments, no bodily fluid is present (or if insufficient body fluid is present) and the applied hemostatic product can be "activated" by wetting, e.g. by spraying, or by otherwise applying a source of moisture (e.g. by exposing the hemostatic product to a moist material such as a sponge), or dropping hemostatic products into a liquid (e.g. a body of water), to cause release of the agents of interest associated with the dextran fibers.

Due to the small footprint and light-weight characteristics of the hemostatic products, they are ideal for situations where space and weight of supplies are at a premium. Examples of such situations include but are not limited to: military operations where the weight and size of the components of a soldier's gear are an issue; in first aid kits; for emergency care during travel (e.g. during space flight, camping, etc.); etc.

The hemostatic products may be used in a variety of situations and for a variety of purposes in which space and weight are not considerations. For example, the hemostatic products of the invention provide a convenient means to administer thrombin and fibrinogen to surgical wounds in a conventional operating theater.

The hemostatic products of the invention may also be advantageously utilized whenever it is desired to package and eventually release one or more dried substances, but where it is unfeasible or undesirable to handle the dried substances directly, e.g. where the quantity is extremely small, or the substance is toxic.

In such cases, the electrospun dextran fibers of the invention may serve as a "scaffolding" or carrier for containing, storing and/or transporting the substance(s) until use, i.e. until contacted with liquid that dissolves the electrospun dextran fibers, concomitantly releasing the substances into the liquid. Such substances may include, for example, enzymes or their precursors (e.g. pro-enzymes or zymogens) and their substrates, substances that activate a protein or enzyme (e.g. proteases, cofactors, etc.), and the like.

The invention also relates to the use of stabilizers that resist the premature degradation of the components utilized in the hemostatic product. The stabilizer also enhances the usable shelf life of the hemostatic product. In certain embodiments, the stabilizer provides the hemostatic product with a shelf life of at least about 2 years. In other embodiments, the hemostatic product exhibits a shelf life of at least 3 years.

As used herein, the term usable shelf life means that the hemostatic product does not exhibit noticeable degradation when viewed without magnification or with magnification such as a magnifying glass or microscope.

One such stabilizer is adapted for use in conjunction with thrombin. It is believed that the thrombin stabilizer gets into the structure of the thrombin and thereby reduces the rate at which the thrombin breaks down. The at least one thrombin stabilizer may be mixed with the thrombin before the thrombin is mixed with the other components used to fabricate the hemostatic product.

In one embodiment, the thrombin stabilizer contains a sugar such as sucrose. In certain embodiments, the sucrose is used in the thrombin stabilizer at a concentration of up to about 5 percent by weight of the thrombin. In other embodiments, the sucrose concentration is about 1 percent by weight of the thrombin.

Prior to mixing the thrombin stabilizer with the thrombin, the thrombin stabilizer may be mixed with dextran. It is believed that the dextran enhances the ability of the sucrose to enter into the structure of the thrombin.

In certain embodiments, the dextran is used in the thrombin stabilizer at a concentration of up to about 5 percent by weight of the thrombin. In other embodiments, the dextran concentration is about 1 percent by weight of the thrombin.

Similarly, a stabilizer may be used in conjunction with the fibrinogen. Prior to applying the fibrinogen to the other components of the hemostatic bandage, the fibrinogen stabilizer may be mixed with the fibrinogen. It is believed that the fibrinogen stabilizer gets into the structure of the fibrinogen and thereby reduces the rate at which the fibrinogen breaks down.

In one embodiment, the fibrinogen stabilizer contains a sugar such as sucrose. In certain embodiments, the sucrose is used in the fibrinogen stabilizer at a concentration of up to about 5 percent by weight of the fibrinogen. In other embodiments, the sucrose concentration is between about 2 and 3 percent by weight of the fibrinogen. In still other embodiments, the sucrose concentration is about 1 percent by weight of the fibrinogen.

Prior to mixing the fibrinogen stabilizer with the fibrinogen, the fibrinogen stabilizer may be mixed with a solubility enhancing agent. It is believed that the solubility enhancing agent enhances the ability of the sucrose to enter into the structure of the fibrinogen. In certain embodiments, the solubility enhancing agent is a detergent. In other embodiments, the solubility enhancing agent is Pluronic.

In certain embodiments, the solubility enhancing agent is used in the fibrinogen stabilizer at a concentration of up to about 1 percent by weight of the fibrinogen. In other embodiments, the solubility enhancing agent concentration is about 0.002 percent by weight of the fibrinogen.

In another embodiment of the invention, the fibrinogen and thrombin are placed on the surface of and/or integrated into the matrix of a dissolving film. Using the fibrinogen and thrombin in such a configuration enables the hemostatic product to be positioned over the position on the person's body where the blood is being emitted and, as such, where hemostasis is desired.

The dissolvable film may be configured to dissolve relatively quickly when exposed to liquid such as blood. In certain embodiments, the film dissolves in less than about 30 seconds. In other embodiments, the film dissolves in less than about 5 seconds. An example of one suitable dissolving film is marketed by Hughes Medical Corp.

An example of another dissolving film is a dissolving paper that is fabricated from materials that do not pose a health hazard to the patient after the dissolving paper has dissolved. In certain embodiments, the dissolving paper may be fabricated from a material that enhances the ability of at least one of the fibrinogen and thrombin to achieve hemostasis. An example of one such dissolving paper is marketed by Daymark Technologies.

In another embodiment, the fibrinogen and thrombin are provided between two layers of a dissolvable material. An example of one such suitable dissolving film is marketed by Hughes Medical Corp. and which is discussed above.

The fibrinogen and thrombin may be provided in a variety of configurations using the concepts of the invention. In one such configuration, at least one of the fibrinogen and the thrombin are provided in a powder that is retained between the layers of the dissolvable material.

The dissolvable material should have sufficient structural integrity to retain the fibrinogen and thrombin therebetween while resisting interaction with the fibrinogen and thrombin. The dissolvable material should also dissolve relatively quickly when exposed to liquids such as blood such that the fibrinogen and thrombin are released therefrom.

As used herein, "quickly dissolving" means that the dissolvable material breaks down to a sufficient extent such that a significant portion of the fibrinogen and thrombin are in contact with the blood in less than about 30 seconds. In other embodiments, the dissolvable material breaks down in less than about 10 seconds.

The dissolvable material should also facilitate readily bonding such that two layers of the dissolvable material can be attached together around the edges thereof to thereby form an enclosure that is adapted to retain the fibrinogen and thrombin therein.

An example of one suitable technique for attaching the dissolvable materials to each other is applying a small amount of liquid to at least one of the pieces of material that are intended to be bonded together. The water causes a slight breakdown of the dissolvable materials such that when two layers of the dissolvable material are placed adjacent to each other, the layers of the dissolvable material bond together.

The dissolvable material may be fabricated from a variety of materials. The dissolvable material should not negatively impact the stability of the fibrinogen and thrombin. The material used to fabricate the dissolvable layer should also be selected to not have any adverse health effects on the person or animal on which the product is intended to be used.

In certain embodiments, the material used to fabricate the hemostatic product may alone or in conjunction with the fibrinogen or thrombin enhance the rate of hemostasis. Examples of components that may be used for the dissolvable material include cellulose derived materials.

In one configuration, a separate device is used to maintain the hemostatic product in a desired position with respect to the patient. An example of one such device is gauze that is wrapped around the portion of the body that is bleeding.

In another configuration, at least a portion of the hemostatic product is covered with an adhesive. The adhesive may be positioned around at least a portion of an edge of the hemostatic product. In an alternative configuration, the adhesive covers a substantial portion of an inner surface of the hemostatic product.

In such a configuration where the adhesive is likely to come into contact with the portion of the patient's body that is bleeding, the adhesive should be selected to be biocompatible to minimize the potential of the patient experiencing complications caused by contact between the adhesive and the tissue that is bleeding.

In another embodiment, the fibrinogen and thrombin may be placed inside of an enclosure and/or on the surface of an enclosure that does not dissolve when exposed to liquids such as blood. Such a configuration may facilitate forming a blood clot thereon such that the blood clot could be removed from the patient.

Such a configuration may be similar to a conventional tea bag in that the enclosure may be attached to a string that is used in conjunction with at least one of positioning the product proximate an area where hemostasis is desired or removing the product and the associated blood clot from the patient.

The string may be fabricated from a material that is sufficiently strong such that the string does not break either when positioning the product or when removing the product from the patient. The string should also be fabricated from a material that is not likely to produce adverse biological interactions.

The enclosure may be configured to discharge the fibrinogen or thrombin over a selected period of time. The rate at which the fibrinogen and thrombin are discharged may be adjustable based upon the rate and/or volume of blood that is being discharged from the patient.

In an alternative configuration, the enclosure may be configured to breakdown over an extended period of time. As the enclosure breaks down, the fibrinogen and thrombin may be discharged from the product.

By controlling the rate at which the fibrinogen and thrombin are discharged from the product and/or the rate at which the enclosure degrades, the product minimizes the formation of a clot having a relatively large size but rather may facilitate the formation of a plurality of clots having a smaller size. Such smaller clots may be more readily broken down within the body than if relatively large clots were caused to be formed.

This configuration of the hemostasis product may be particularly suited for use in conjunction with bleeding in patients that while being within a bodily cavity such a bodily cavity is accessible from outside of the body. Examples of surgical techniques with which the hemostasis product may be used in conjunction include sinus and tonsil surgery.

In another embodiment, the fibrinogen and thrombin are compressed into a tablet. In addition to the fibrinogen and thrombin, the tablet may also include at least one excipient. The excipient should facilitate not only holding together the fibrinogen and thrombin as well as promoting relatively quickly dissolving of the tablet.

As used herein, the term "relatively quickly" means that the tablets dissolve when placed in a liquid in less than about 30 seconds. In other configurations, the tablets dissolve in less than about 10 seconds. Quickly dissolving the tablets enables the fibrinogen and the thrombin to be quickly released from the tablets such that these materials may provide rapid hemostasis.

Additionally, in certain embodiments, the excipients that are used in formulating the tablets should not decrease the stability and/or solubility of the fibrinogen and the thrombin. In certain embodiments, the excipients used in formulating the tablets should increase the stability of the fibrinogen and thrombin.

An example of one such excipient is sorbitol, which has been formed into small particles such as by using spray-drying. In one such configuration, the particles have a generally spherical shape and have a generally uniform size.

The spray-dried sorbitol particles not only provide advantageous flowability characteristics but also exhibit desirable compactability characteristics when forming the tablets using a direct compression technique.

Additionally, the spray-dried sorbitol particles provide good solubility for release of the fibrinogen and thrombin from the tablets. An example of one such spray-dried sorbitol particle is marketed by SPI Pharma under the designation SORBITAB SD 250.

Another excipient that may be used in fabricating the tablets is mannitol, which has been formed into small particles such as be using spray drying. The particles may be formed with a narrow particle size distribution, which reduces the potential of the components segregating while the tablets are being formed.

An advantage of the mannitol is that this material is non-hydroscopic such that the mannitol does not add moisture to the other components used in the tablets or contribute to moisture pickup either during the process of forming the tablets or after the tablets have been formed. The mannitol thereby protects the water-sensitive fibrinogen and thrombin.

The spray-dried mannitol particles not only provide advantageous flowability characteristics but also exhibit desirable compactability characteristics when forming the tablets using a direct compression technique.

The spray-dried mannitol particles also promote rapid disintegration or dissolvability of the tablets such that the fibrinogen and thrombin can be quickly released from the tablets. An example of one such spray-dried mannitol particle is marketed by SPI Pharma under the designation MANNOGEM EZ.

Other materials that may be used as excipients when preparing the tablets include fructose and maltose. Similar to the other excipients that are discussed above, the preceding excipients may be formed into small particles before being used mixed with the other components that are used in the tablets.

Another excipient that may be used in conjunction with fibrinogen and thrombin is a quick dissolving platform that is marketed under the designation PHARMABURST 500 by SPI Pharma. This material provides the tablets with the ability to be rapidly dissolved while also providing desirable characteristics for compaction and friability.

Depending on the excipient that is used in the tablet, it may also be desirable to use a lubricant when preparing the tablet. The lubricant may enhance the physical properties of the tablets. Examples of such physical properties include brittleness, friability and hardness. An example of one such lubricant is sodium stearyl fumarate, which is available from SPI Pharma under the designation LUBRIPHARM.

The concentration of the lubricant that is used in fabricating the tablets may depend on a variety of factors such as the types of excipients that are used. In certain embodiments, the concentration of the lubricant is up to about 5 percent by weight. In other embodiments, the concentration of the lubricant is between about 2 and 3 percent by weight.

In still other embodiments, the concentration of the lubricant is about 2.5 percent by weight.

Once the components are mixed together, the mixture is subjected to compression, which thereby causes the components to form the tablets. In certain embodiments, the compressive force is at least 5,000 psi. In other embodiments, the compressive force is between about 10,000 psi and about 12,000 psi.

When preparing the tablets using the preceding process, it may not be necessary to include dextran. Even though dextran may not be required, it is possible to use dextran along with the other components that are used to formulate the tablets.

In another embodiment of the invention, the fibrinogen and thrombin may be incorporated into a fast dissolving tablet such as by using technology marketed by Catalent Corporation under the designation Zydis.

The fast dissolving tablets dissolve in less than 30 seconds and, in some configurations, dissolve in less than about 5 seconds. Quickly dissolving the tablets is important because at the tablets dissolve, the fibrinogen and thrombin contained therein is released and can thereby produce hemostasis.

The amount of the fibrinogen and thrombin used in the tablet may be selected based upon the volume of bleeding. In certain embodiments, there is up to about 1 gram of fibrinogen and thrombin in each of the tablets. In other embodiments, there is about 500 micrograms of fibrinogen and thrombin in each of the tablets.

In another embodiment of the invention, the fibrinogen and thrombin are applied to a surface of or incorporated into an applicator. Such an applicator enables the fibrinogen and thrombin to be accurately delivered to an area where hemostasis is desired.

In one such configuration, the applicator has an elongated portion that may be grasped by a person who is using the hemostatic product. The applicator may have a configuration that is similar to a swab. This configuration of the hemostatic product is particularly suited for locations that are difficult to directly reach. An example of one such condition that this hemostatic product may be used to treat is epistaxis.

At least one of the fibrinogen and thrombin may be electrospun either alone or with another component such as dextran. The fibers produced using such a process may be wrapped around a distal end of the applicator.

The applicator may be configured to release the fibrinogen and thrombin once the hemostatic product encounters blood. Using such a process, the fibrinogen and thrombin would cause clots to form. The clots could be removed from the patient. If the clots are sufficiently small, the clots may be allowed to remain in the patient such that the clots could eventually be broken down.

In another configuration of this hemostatic product, at least one of the fibrinogen and thrombin may be configured to remain relatively close to or be confined to the applicator such that when the fibrinogen and thrombin cause at least one clot to form, such clots remain attached to the applicator. This configuration facilitates removal of the clots from the patient and may be desirable where the clots are likely to be sufficiently large to make it undesirable for the clots to remain in the body.

To facilitate the fibrinogen and thrombin not being released from the applicator, the fibrinogen and thrombin may be incorporated into a material that is attached to an end of the applicator. An example of one such material is foam. The foam may be either open cell foam or closed cell foam. The foam should have pores that are sufficiently large to receive the fibrinogen and thrombin. The foam should not have a strong affinity for either fibrinogen or thrombin so that when the fibrinogen and thrombin are exposed to water, these components are released from the foam.

In another embodiment of the invention, the fibrinogen and thrombin are incorporated into foam. An example of one such suitable foam is an absorbable gelatin sponge such as is available under the designation VETSPON from Novartis.

Depending on the application at which it is desired to use the hemostatic sponge, it may be desirable to prewet the hemostatic sponge prior to the hemostatic sponge being applied to the region where hemostasis is desired.

Another advantage of using the foam is that the foam may be configured to be bendable so that the hemostatic foam can be bent into a configuration that conforms to the shape of the region in which the hemostasis is desired. Once the hemostatic foam is bent into the desired configuration, it may remain in that configuration even without a fastening device being used to hold the hemostatic foam in the desired shape and/or position.

Similar to the foam that is described above, the foam may be either open cell foam or closed cell foam. The foam should not have a strong affinity for either fibrinogen or thrombin so that when the fibrinogen and thrombin are exposed to water, these components are released from the foam.

The fibrinogen and thrombin may be incorporated into the components that are used to fabricate the foam such that rather than the fibrinogen and thrombin being applied to a surface of the foam, the fibrinogen and thrombin are dispersed through the matrix of the foam.

Such a configuration facilitates ongoing release of the fibrinogen and thrombin from the foam and may be particularly beneficial when it is desired to form a clot in a region of the body that is likely to experience rebleeding.

The quick dissolving tablets are suited for use in a variety of applications. An example of one such application is oral bleeding. If the product is intended for use in conjunction with oral bleeding, the tablet may be flavored.

In conjunction with various surgical techniques, it is necessary to form an incision in the patient. Once the surgery is complete, it is necessary for sutures or staples to be used to close up the incision. While the sutures or staples are effective at holding together the tissue, these closure mechanisms are not always effective to stop blood from flowing out through the incision.

The hemostatic product may be placed over at least a portion of the suture line through which blood is passing. The fibrinogen and thrombin contact such blood and thereby provide hemostasis.

Vascular access devices are used in conjunction with a variety of medical treatments such as delivering chemotherapy drugs to a patient. In one configuration, the vascular access devices are surgically implanted in a large vein that is near the patient's heart. The vascular access devices may be left in place for an extended period of time such as more than a year.

One challenge of surgically implanting the vascular access devices is stopping the bleeding around the vascular access device. For example, the blood may leak out of the suture lines or around the conduit. In some situations where it is not possible to stop the leak, it is necessary to bring the patient back to the operating room in an effort to stop the leak.

The hemostatic product may be placed around the vascular access device. Insertion of the vascular vascular access device into the body causes bleeding. The bleeding dissolves at least a portion of the hemostatic product to thereby cause hemostasis upon contact between the blood and the fibrinogen and thrombin that are released by the dissolving of the hemostatic product. Depending on the shape of the vascular access device, it is possible for the hemostatic product to have a variety of configurations.

In other situations, the conduit associated with the vascular access device may be porous. The hemostatic product may be used to provide hemostasis and thereby prevent blood from passing through the porous conduit.

One or more of the preceding configurations of the hemostatic product may be suited for use to stop bleeding from a patient such as when a catheter is removed from a femoral artery in the patient. In such a configuration, the hemostatic product may include an adhesive, which holds the hemostatic product in place while hemostasis is occurring.

Aortic root surgery is used to treat a dilation or enlargement of the aorta. Because of the nature of the aorta, hemostasis plays an important role in the success of the procedure. One of the configurations of the hemostatic product that are discussed above may be used to provide the hemostasis without causing constriction of the aorta, which frequently results from the prior art agents that are used to provide hemostasis in conjunction with this type of surgery.

For wounds that are deeper into the patient, it may be desirable to use the hemostatic product in the form of a pledget that is placed at least partially into the wound and which thereby causes hemostasis within the wound.

In yet another configuration, the hemostatic product may be provided in an elongated configuration such as a tampon-type shape. The hemostatic product could also be formed in the shape of a worm or rope. Such configurations could be used for hemostasis after vaginal surgeries. These configurations could also be used in conjunction with an elongated hole in the patient such as may be caused by a gunshot wound.

The cylindrical configuration of the hemostatic product is also suitable for use in situations where there is a large opening in tissue. In such situations, multiple cylindrical hemostatic products may be inserted into the large opening to thereby fill a portion of such opening.

The facilitate administering the elongated hemostatic product, it may be desirable for the hemostatic product to be stored in an applicator such as a plunger. The plunger could be used to insert the elongated hemostatic product into the wound in the patient.

In another configuration of the hemostatic product, each of the components of the hemostatic product are package separately such as in a syringe. Such a configuration enables the components to be dispensed at different rates so that the hemostasis may be customized to the particular patient or for a particular type of wound. The applicator may allow each of the components to be delivered alternatively or simultaneously.

The hemostatic product may consist substantially of the fibrinogen, thrombin and a carrier that are adapted to be bioabsorbed. Alternatively, the fibrinogen and thrombin may be placed on an outer surface of the hemostatic product such that the hemostatic product would be removed from within the patient after hemostasis is completed.

In yet another configuration, the fibrinogen and thrombin are delivered via an aerosol. The fibrinogen and thrombin may be provide in the form of microspheres that are capable of being dispensed using an aerosol container.

It is also possible to use the hemostatic product in conjunction with robotic surgical procedures. While robotics provide the ability for surgical procedures to be performed by a surgeon who is at a location that is remote to where the patient is located, the robotics have certain limitations. The hemostatic product may be used in conjunction with the robotic surgical procedures to provide hemostasis and thereby overcome such limitations.

In addition to being used to produce hemostasis in humans, the concepts of the invention may be adapted for use in conjunction with other animals. Examples of such animals on which the invention can be used include dogs and cats.

In another embodiment of the invention, an effective amount of water is mixed with dextran to form an aqueous dextran solution. Thereafter, the aqueous dextran solution is electrospun to form a dextran sheet.

The dextran sheet may be stored until it is desired to fabricate the hemostatic product. In one such configuration, the dextran sheet is rolled. Rolling of the dextran sheet not only reduces the area taken up by the dextran sheet while the dextran sheet is being stored but also reduces the potential that the dextran sheet will be damaged prior to fabricating the hemostatic product.

When the dextran sheet is being rolled, care should be exercised to not roll the dextran sheet too tightly because such a process would increase the density of the dextran sheet. Alternatively, tightly rolling the dextran sheet may be desired to increase the density of the dextran sheet prior to fabricating the hemostatic product.

The thrombin and fibrinogen are mixed together at the ratio discussed in the other portions of this patent application just before it is desired to fabricate the hemostatic product. The mixing should provide a relatively uniform dispersion of the thrombin and fibrinogen in the mixture.

In certain embodiments, the thrombin is dispersed on the dextran sheet to provide a thrombin concentration of between about 2 and 200 NIH Units of thrombin per square centimeter of the dextran sheet.

In certain embodiments, the fibrinogen is dispersed on the dextran sheet to provide a fibrinogen concentration of between about 20 and 60 grams of fibrinogen per square centimeter of the dextran sheet.

The dextran sheet is unrolled and the thrombin and fibrinogen mixture is dispersed over the surface of the dextran sheet. In certain embodiments, the thrombin and fibrinogen mixture is dispersed in a substantially uniform manner over the surface of the dextran sheet. This even dispersion is desired because it enables each portion of the hemostatic product to have a substantially hemostatic activity.

This process is repeated and the sheets are stacked until the hemostatic product exhibits a desired amount of hemostatic activity. In certain embodiments, the hemostatic product includes between about 2 and 20 dextran layers.

The thrombin and fibrinogen mixture is not placed on the uppermost layer of the dextran sheet. Using this configuration, the thrombin and fibrinogen are located at an interior location in the hemostatic product. Fabricating the hemostatic product in this manner enhances the ability to retain thrombin and fibrinogen inside of the hemostatic product even though the thrombin and fibrinogen are sprinkled on the surface of the dextran sheet.

While it is possible to put thrombin and fibrinogen on the outside of the hemostatic product, a portion of the thrombin and fibrinogen may become dissociated from the hemostatic product prior to use. In view of the cost of thrombin and fibrinogen, it is desirable for substantially all of the thrombin and fibrinogen to remain associated with the hemostatic product until it is desired to use the hemostatic product to maximize the efficacy of the hemostatic product.

Even though the thrombin and fibrinogen are mixed together prior to placing the thrombin and fibrinogen on the dextran sheet, the thrombin and fibrinogen are sufficiently dispersed on the dextran sheet so that the thrombin and fibrinogen do not react prior to placing the hemostatic product at the location where hemostasis is desired.

The hemostatic product is then cut into pieces. In certain embodiments, the pieces may be formed in a generally square shape. The size of the pieces may be selected based upon the intended use of the hemostatic product. For example, when the hemostatic product is intended for surgical applications, the pieces may have a smaller size than if the hemostatic product is intended for trauma applications.

A cutter may be used to cut the hemostatic product into the desired size. In addition to cutting the hemostatic product into pieces, the cutter may cause the layers of the dextran sheets that are adjacent to the cutter to be compressed together. This compression causes the dextran layers to stay together.

In certain embodiments, the pieces of the hemostatic product are vacuum packaged. In addition to maintaining the hemostatic product sterile, the vacuum packaging also compresses the layers in the hemostatic product, which enhances the ability of the layers to resist separation after the hemostatic product is removed from the package prior to use.

This process thereby enhances the ability to use the hemostatic product because the layers in the hemostatic product resist coming apart. An advantage of using this process is that no additional steps are necessary to retain the layers together. Additionally, it does not require the use of additional components and/or additional processing steps, which could affect the efficacy of the hemostatic product.

EXAMPLES

Dextran is mixed with an effective amount of water to form an aqueous dextran solution. The aqueous dextran solution is electrospun to form an electrospun dextran sheet.

Thrombin and fibrinogen were mixed together and then dispersed on the electrospun dextran sheet. The thrombin was dispensed at a rate of between about 1.3 and 2.7 NIH Units per square centimeter of the electrospun dextran sheet. The fibrinogen was dispensed at a rate of between about 3.6 and 7.4 milligrams per square centimeter of the electrospun dextran sheet This process was repeated until there were 8 layers of the electrospun dextran sheet in a stacked configuration. The thrombin and fibrinogen mixture was not dispersed on the surface of the uppermost layer. The electrospun dextran sheet has a thickness of between about 1 and 3 millimeters.

A cutter was then used to cut the hemostatic product into pieces having a width of about 4.8 centimeters and a length of about 4.8 centimeters. In addition to forming pieces of a desired size, the cutting causes the electrospun dextran layers to be pushed together. This process caused the electrospun dextran layers to resist separation. The pieces of the hemostatic product were vacuum packaged for storage until use. In addition to preventing contamination of the hemostatic product, the vacuum packaging caused the layers of the electrospun dextran to be urged together.

A commercially available absorbable fibrin sealant product marketed under the designation TACHOSIL (Nycomed) was used to compare with the performance of the hemostatic product described in this patent application.

The TACHOSIL product contains an equine collagen sponge that is coated on one side thereof with the thrombin and fibrinogen. The TACHOSIL product contains between 3.6 and 7.4 milligrams of human fibrinogen per square centimeter of the product and between 1.3 and 2.7 NIH Units of human thrombin per square centimeter of the product.

Utilizing the preceding information regarding the concentration of thrombin and fibrinogen on the TACHOSIL product, the TACHOSIL product was cut into square pieces to provide an amount of thrombin and fibrinogen on each piece of the TACHOSIL product that was approximately equal to the amount of thrombin and fibrinogen on the hemostatic product that was prepared above.

The hemostatic efficacy of the hemostatic product of this patent application and the TACHOSIL product was evaluated using the swine liver injury model, which has previously been used to evaluate hemostatic efficacy. The swine liver injury model enables multiple tests to be conducted on a single animal.

The tests were conducted using adult, domestic, breed-indifferent, female pigs having a weight of between about 50 and 70 kilograms. Each animal was subjected to an initial examination to verify the animal was in good health. Prior to the procedure, the animals were quarantined for three days during which the animals were provided food and water ad libitum.

Prior to initiating the procedure, anesthesia was administered to the animal. During the procedure, anesthesia and fluid maintenance was administered to the animal. A heating pad was placed under the animal during the procedure to assist in maintaining the animal's body temperature during the procedure.

A midline laparotomy was performed to provide access to the abdominal organs where the hepatic biopsies were to be performed. A biopsy punch having a diameter of approximately 8 millimeters was used to create each hepatic biopsy. The hepatic biopsies each have a width of about 8 millimeters and a depth of about 4 millimeters. The cylindrical hepatic biopsy was surgically removed with a scissor.

The presence of continuous free bleeding at the biopsy site was observed for about 20-25 seconds. Thereafter, the hemostatic product was applied to the biopsy site. The hemostatic hemostatic product was held in place with manual pressure for about 20 seconds.

The manual pressure was then removed while leaving the hemostatic product on the biopsy site. The biopsy site was observed for about 2 minutes for visible signs of active bleeding.

If bleeding persisted, an additional hemostatic product was placed over the biopsy site. The hemostatic product was held in place with manual pressure for about 20 seconds. Thereafter, the manual pressure was removed while leaving the hemostatic product on the biopsy site. The biopsy site was observed for about 2 minutes for visible signs of active bleeding. This process was repeated for up to 4 times if the bleeding had not previously stopped.

As a control, the biopsy punch was used to create a hepatic biopsy having a width of about 8 millimeters and a depth of about 4 millimeters. The biopsy was observed for about 2 minutes. During this time period, the biopsy did not stop bleeding.

Tests using the hemostatic product of this patent application, the TACHOSIL product and the control were performed in a random order to minimize the potential effect caused by the order in which the hemostatic product was used during the evaluation.

The order in which the evaluation of the hemostatic agents was performed and the results obtained from such evaluations are set forth in Table 1 below.

TABLE 1

| Hemostasis agent | Number of compressions to achieve hemostasis | Time to achieve hemostasis (minutes) |
|---|---|---|
| Tachosil | 2 | 4 |
| This invention | 1 | 2 |
| This invention | 2 | 4 |
| Control | n/a | n/a |
| Tachosil | 4 | 8 |
| Control | n/a | n/a |
| This invention | 1 | 2 |
| Tachosil | 2 | 4 |

The evaluation was repeated using 5 additional animals. The order in which the hemostatic products were used on the 5 additional animals was also randomized.

The results from the first evaluation set forth in Table 1 were combined with the results from the 5 additional animals. There were a total of 18 samples for each the hemostatic product from this patent application and the TACHOSIL product.

For these 18 samples, the mean time for the hemostatic product from this patent application to cause hemostasis was 2.9 minutes with a standard deviation of 1.7 minutes. For these 18 samples, the mean time for the TACHOSIL product to cause hemostasis was 4.7 minutes with a standard deviation of 1.4 minutes. The hemostatic product from this patent application thereby provided a reduction in time to achieve hemostasis of nearly two minutes.

The animal blood was evaluated prior to the biopsy and after hemostasis was achieved for potential changes in the hematology. There were no significant differences in the hematology results for the hemostatic product from this patent application and the TACHOSIL product.

The clots provided by the hemostatic product of this patent application were compared to the clots provided by the TACHOSIL product using pathology. Fibrin was identifiable in all of the biopsies treated with the hemostatic product of this patent application. On the other hand, fibrin was not identifiable in 5 out of 18 biopsies treated with the TACHOSIL product.

The total number of biopsies needing additional compressions for the hemostatic product of this patent application was 5. The total number of biopsies needing additional compressions for the TACHOSIL product was 17. The hemostatic product of this patent application thereby represents a reduction of biopsies needing additional compressions of over 70% as compared to the TACHOSIL product.

The total number of additional compressions needed to provide hemostasis with the hemostatic product of this patent application was 8. The total number of additional compressions needed to provide hemostasis for the TACHOSIL product was 24. The hemostatic product of this patent application thereby represents a reduction of additional compressions of over 60% as compared to the TACHOSIL product.

The "basketweave" configuration of the hemostatic product of this patent application allowed entrapment of erythrocytes dispersed throughout the biopsy site. On the other hand, the TACHOSIL product resulted in trapping of sheets of erythrocytes at the base of the biopsy site or between areas of amorphous implant material.

Because the thrombin and fibrinogen used in the TACHOSIL product are obtained from human plasma, there is a risk that the TACHOSIL product may contain infectious agents. Another advantage of the hemostatic product of the current invention over the TACHOSIL is that the hemostatic product of the current invention appears to remain stable at a higher temperature than the TACHOSIL product.

While a direct comparison was not conducted, the electrospun dextran base used in the hemostatic product produced according to this invention rapidly dissolves upon contact with fluids. The dextran is absorbed into the body in a relatively short time frame that ranges from minutes to a few days. The rapid depletion of the dextran carrier can provide beneficial results in conjunction with reducing the risk of inflammation and scaring.

In contrast, the collagen sponge used in the TACHOSIL product breaks down over a much longer period of time such as up to about 4 months. This aspect of the TACHOSIL product is indicated by the manufacturer to be a feature because it is indicated that the collagen sponge holds fibrin clots to the wound surface to achieve hemostasis. The slow absorption of collagen can be associated with increased risk of inflammation and scaring.

The electrospun dextran used in the hemostatic product provides this hemostatic product with a higher level of flexibility compared to the collagen sponge used in the TACHOSIL product. This enhanced flexibility enables the hemostatic product described in this patent application to more readily conform to the surface of the wound than the TACHOSIL product.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of achieving hemostasis as a hemostatic vascular access device is inserted into a body, wherein the method comprises:
   forming a hemostatic vascular access device comprising:
      mixing dextran and water to form a dextran-water mixture;
      forming the dextran-water mixture into a first support layer;
      mixing fibrinogen and thrombin to form a fibrinogen and thrombin mixture;
      dispersing the fibrinogen and thrombin mixture on the first support layer to form a hemostatic sheet; and
      placing the hemostatic sheet at least half way around a vascular access device;
   inserting at least a portion of the hemostatic vascular access device into the body, wherein the inserting step causes bleeding;
   dissolving at least a portion of the hemostatic sheet when contacted with blood; and
   achieving hemostasis when the fibrinogen and thrombin contact the blood.

2. The method of claim 1, the dextran is mixed with the water at a concentration of between about 3 and 9 grams of dextran to about 6 milliliters of water.

3. The method of claim 1, and further comprising mixing at least a portion of the thrombin into the dextran-water mixture prior to forming the dextran-water mixture into the first support layer.

4. The method of claim 1, wherein the first support layer has a relatively uniform thickness.

5. The method of claim 1, wherein the thrombin is salmon thrombin and wherein the fibrinogen is salmon fibrinogen.

6. The method of claim 1, wherein forming the first support layer comprises electrospinning the dextran-water mixture to form a fiber and depositing the fibers are least partially on top of each other.

7. The method of claim 1, and further comprising compressing the first support layer to a height that is less than an initial height of the first support layer, wherein the compression causes the height of the first support layer to be reduced by at least 75 percent compared to the initial height of the first support layer.

8. The method of claim 1, and further comprising placing a retaining mechanism over a surface of the hemostatic sheet on which the fibrinogen and thrombin mixture has been dispersed, wherein the retaining mechanism retains the fibrinogen and thrombin mixture on the hemostatic sheet.

9. The method of claim 8, wherein the retaining mechanism is a second support layer having a configuration that is similar to the first support layer.

10. The method of claim 1, and further comprising dispensing at least one bioactive agent on the hemostatic sheet.

11. The method of claim 1, wherein the first support layer is formed on a support material and wherein the support material comprises compressed electrospun dextran.

12. A method of achieving hemostasis as a hemostatic vascular access device is inserted into a body, wherein the method comprises:
   forming a hemostatic product comprising:
      mixing dextran and water to form a dextran-water mixture;
      mixing thrombin into the dextran-water mixture to form a dextran-thrombin-water mixture;
      forming the dextran-thrombin-water mixture into a first support layer;
      dispersing fibrinogen on the first support layer to form a hemostatic sheet; and
      placing the hemostatic sheet at least half way around a vascular access device;
   inserting at least a portion of the hemostatic vascular access device into the body, wherein the inserting step causes bleeding;
   dissolving at least a portion of the hemostatic sheet when contacted with blood; and
   achieving hemostasis when the fibrinogen and thrombin contact the blood.

13. The method of claim 12, the dextran is mixed with the water at a concentration of between about 3 and 9 grams of dextran to about 6 milliliters of water.

14. The method of claim 12, and further comprising mixing at least a portion of the thrombin into the dextran-water mixture prior to forming the dextran-water mixture into the first support layer.

15. The method of claim 12, wherein the first support layer has a relatively uniform thickness.

16. The method of claim 12, wherein the thrombin is salmon thrombin and wherein the fibrinogen is salmon fibrinogen.

17. The method of claim 12, wherein forming the first support layer comprises electrospinning the dextran-thrombin-water mixture to form a fiber and depositing the fibers are least partially on top of each other.

18. The method of claim 12, and further comprising compressing the first support layer to a height that is less than an initial height of the first support layer, wherein the compression causes the height of the first support layer to be reduced by at least 75 percent compared to the initial height of the first support layer.

19. The method of claim 12, and further comprising placing a retaining mechanism over a surface of the hemostatic sheet on which the fibrinogen has been dispersed, wherein the retaining mechanism retains the fibrinogen on the hemostatic sheet.

20. The method of claim 19, wherein the retaining mechanism is a second support layer having a configuration that is similar to the first support layer.

21. The method of claim 12, and further comprising dispensing at least one bioactive agent on the hemostatic sheet.

22. The method of claim 12, wherein the first support layer is formed on a support material and wherein the support material comprises compressed electrospun dextran.

23. A method of achieving hemostasis as a hemostatic vascular access device is inserted into a body, wherein the method comprises:
    forming a hemostatic vascular access device comprising:
        mixing dextran and water to form a dextran-water mixture;
        electrospinning the dextran-water mixture into a first support layer;
        dispersing antibiotics, medicaments that alleviate pain, growth factors, bone morphogenic proteins, vasoactive materials, inflammation reduction steroids and combinations thereof on the first support layer to form a hemostatic sheet; and
        placing the hemostatic sheet at least half way around a vascular access device; and
    inserting at least a portion of the hemostatic vascular access device into the body, wherein the inserting step causes bleeding;
    dissolving at least a portion of the hemostatic sheet when contacted with blood; and
    achieving hemostasis when the fibrinogen and thrombin contact the blood.

* * * * *